US007807784B2

(12) United States Patent
Fu

(10) Patent No.: US 7,807,784 B2
(45) Date of Patent: Oct. 5, 2010

(54) INCREASED T-CELL TUMOR INFILTRATION BY MUTANT LIGHT

(75) Inventor: Yang-Xin Fu, Chicago, IL (US)

(73) Assignee: The University of Chicago, Chicago, IL (US)

(*) Notice: Subject to any disclaimer, the term of this patent is extended or adjusted under 35 U.S.C. 154(b) by 545 days.

(21) Appl. No.: 10/865,623

(22) Filed: Jun. 10, 2004

(65) Prior Publication Data
US 2005/0025754 A1  Feb. 3, 2005

Related U.S. Application Data

(60) Provisional application No. 60/477,733, filed on Jun. 11, 2003, provisional application No. 60/478,126, filed on Jun. 12, 2003.

(51) Int. Cl.
A61K 39/00 (2006.01)
C07K 14/00 (2006.01)
(52) U.S. Cl. .................... 530/350; 424/94.1; 424/277.1
(58) Field of Classification Search .................. 530/350
See application file for complete search history.

(56) References Cited

U.S. PATENT DOCUMENTS

| 4,797,368 | A | 1/1989 | Carter et al. |
| 4,980,286 | A | 12/1990 | Morgan et al. |
| 5,399,346 | A | 3/1995 | Anderson et al. |
| 5,436,146 | A | 7/1995 | Shenk et al. |
| 5,994,523 | A | 11/1999 | Kawakami et al. |
| 6,048,551 | A | 4/2000 | Hilfinger et al. |
| 6,140,467 | A | 10/2000 | Ware |
| 6,207,147 | B1 | 3/2001 | Hiserodt et al. |
| 6,475,986 | B1 * | 11/2002 | Aggarwal ..................... 514/12 |
| 6,635,743 | B1 | 10/2003 | Ebner et al. |
| 7,241,576 | B2 | 7/2007 | Aggarwal |
| 2003/0166546 | A1 * | 9/2003 | Aggarwal ..................... 514/12 |

FOREIGN PATENT DOCUMENTS

| WO | WO 01/79496 A2 | 10/2001 |
| WO | WO 02/32463 A1 | 4/2002 |
| WO | WO 02/34780 A2 | 5/2002 |
| WO | WO 03/040307 A2 | 5/2003 |

OTHER PUBLICATIONS

Tamada et al., Nature Medicine, vol. 6, p. 283-289, Mar. 2000.*
Boon, T and van der bruggen, P: (1996) Human tumor antigens recognized by T. lymphocytes. *J. Exp. Med.* 183, 725-729.
Cannon, R.E. et al. (1998). Induction of transgene expression in Tg.AC(v-HA-ras) transgenic mice concomitant with DNA hypomethylation. *Mol Carcinog* 21, 244-250.
Chen, L., Linsley, P.S., and Hellstrom, K.E. (1993). Costimulation of T cells for tumor immunity. *Immunol Today* 14, 483-486.
Cyster, J.G. (1999). Chemokines and cell migration in secondary lymphoid organs. *Science* 286, 2098-2102.

Dougall, W.C. et al. (1999). RANK is essential for osteoclast and lymph node development. *Genes Dev* 13, 2412-2424.
Ettinger, R. (2000). The Role of tumor necrosis factor and lymphotoxin in lymphoid organ development. *Curr Top Microbiol Immunol* 251, 203-210.
Fu, Y.X. & Chaplin, D.D. (1999). Development and maturation of secondary lymphoid tissues. *Annu Rev Immunol* 17, 399-433.
Kang, H.S. et al. (2002). Signaling via LTbetaR on the lamina propria stromal cells of the gut is required for IgA production. *Nat Immunol* 3, 576-582.
Kim, D. et al. (2000). Regulation of peripheral lymph node genesis by the tumor necrosis factor family member TRANCE. *J Exp Med* 192, 1467-1478.
Kong, Y.Y. et al. (1999). Activated T cells regulate bone loss and joint destruction in adjuvant arthritis through osteoprotegerin ligand. *Nature* 402, 304-309.
Leder, A., Kuo, A., Cardiff, R.D., Sinn, E., and Leder, P. (1990). v-HA-ras transgene abrogates the initiation step in mouse skin tumorgenesis: effects of phorbol esters and terinoic acid. *Proc. Natl. Acad. Sci. USA* 87, 9178-9182.
Mauri, D.N. et al. (1998). LIGHT, a new member of the TNF superfamily, and lymphotixin alpha are ligands for herpes virus entry mediator. *Immunity* 8, 21-30.
Melero, I. et al. (1997). Monoclonal antibodies against the 4-1BB T0cell activation molecule eradicate established tumors. *Nat Med* 3, 682-685.
Ochsenbein, A.F. et al. (2001). Roles of tumor localization, second signals and cross priming in cytotoxic T-cell induction. *Nature* 411, 1058-1064.
Ostrand-Rosenberg, S. (1991). Cell-based vaccines for the stimulation of immunity to metastatic cancers. *Immunol Rev* 170, 101-114.
Peace, D.J. et al. (1994). Lysis of ras oncogene-transformed cells by specific cytotoxic T lymphocytes elicited by primary in vitro immunization with mutated ras peptide. *J Exp Med* 179, 473-479.
Rooney, I.A. et al. (2000). The lymphotoxin-beta receptor is necessary and sufficient for LIGHT-mediated apoptosis of tumor cells. *J Biol Chem* 275, 14307-1431.
Rosenberg, I.A. et al. (2001). Progress in human tumor immunology and immunotherapy. *Nature* 411, 380-384.
Ruddle, N.H. (1999). Lymphoid neo-organeogenesis: lymphotoxin's role in inflammation and development. *Immuno Res* 19, 119-125.
Sarma, S. et al. (1999). Cytotoxic T lymphocytes to an unmutated tumor rejection antigen P1A: normal development but restrained effector function in vivo. *J Exp Med* 189, 811-820.

(Continued)

Primary Examiner—Larry R. Helms
Assistant Examiner—Lei Yao
(74) Attorney, Agent, or Firm—Barnes & Thornburg LLP; Alice O. Martin

(57) ABSTRACT

Mutant LIGHT expressed in a tumor environment elicited high levels of chemokines and adhesion molecules, accompanied by massive infiltration of naïve T lymphocytes. Methods and compositions to elicit immune responses against tumors including tumor volume reduction and reduced metastasis using mutant LIGHT are disclosed.

4 Claims, 14 Drawing Sheets

OTHER PUBLICATIONS

Schreiber, H. (1999). Tumor Immunology in *Fundametal Immunology* (ed. Paul, W.E.). Lippincott Rave Press, New York, 1247-1280.

Sha, W.C. et al. (1988). Selective expression of an antigen receptor on CD8-bearing T lymphocytes in transgenic mice. *Nature* 335, 271-274.

Tamada, K. et al. (2000). Modulation of T-cell-mediated immunity in tumor and graft-versus-host disease models through the LIGHT costimulatory pathway. *Nat Medl* 6, 283-289.

Wang, J. et al. (2002). The complementation of lymphotoxin deficiency with LIGHT, a newly discovered TNF family member, for the restoration of secondary lymphoid structure and function. *Eur J Immunol* 32; 1969.

Wang, J. et al. (2001) The regulation of T cell homeostasis and autoimmunity by T cell derived LIGHT. *J clinic. Invest* 108, 1771-1780.

Wick, M. et al. (1997). Antigenic cancer cells grow progressively in immune hosts without evidence for T cell exhaustion or systemic anergy. *J Exp Med* 186, 229-238.

Wu, Q. et al. (1999) The requirement of membrane lymphotoxin for the presence of dendritic cells in lymphoid tissues. *J Exp Med* 190, 629-638.

Ye, Q. et al. (2002) Modulation of LIGHT-HVEM costimulation prolongs cardiac allograft survival. *J Exp Med* 195, 795-800.

Ye, Z et al. (2002) Gene therapy for cancer using single-chain Fv fragments specific for 4-1BB. *Nat Med* 8, 343-348.

Zhai, Y. et al. (1998). LIGHT, a novel ligand for lymphotoxin beta receptor and TR2/HVEM induces apoptosis and suppresses in vivo tumor formation via gene transfer. *Journal of Clinical Investigation* 102, 1142-1151.

Database WPI (2002): "Section Ch, Week 200203," Derwent Publications Ltd., Longdon, GB, AN 2002-026029 (WO01/79496-Abstract).

Database WPI (2003): "Section Ch, Week 200340," Derwent Publications Ltd., Longdon, GB, AN 2003-430659 (WO03/040307-Abstract).

International Search Report issued in PCT/US2004/018631 (2004).

Ware, "Network Communications: Lymphotoxins, Light, and TNF," *Annu. Rev. Immuno.*, 23: 787-819 (2005).

\* cited by examiner

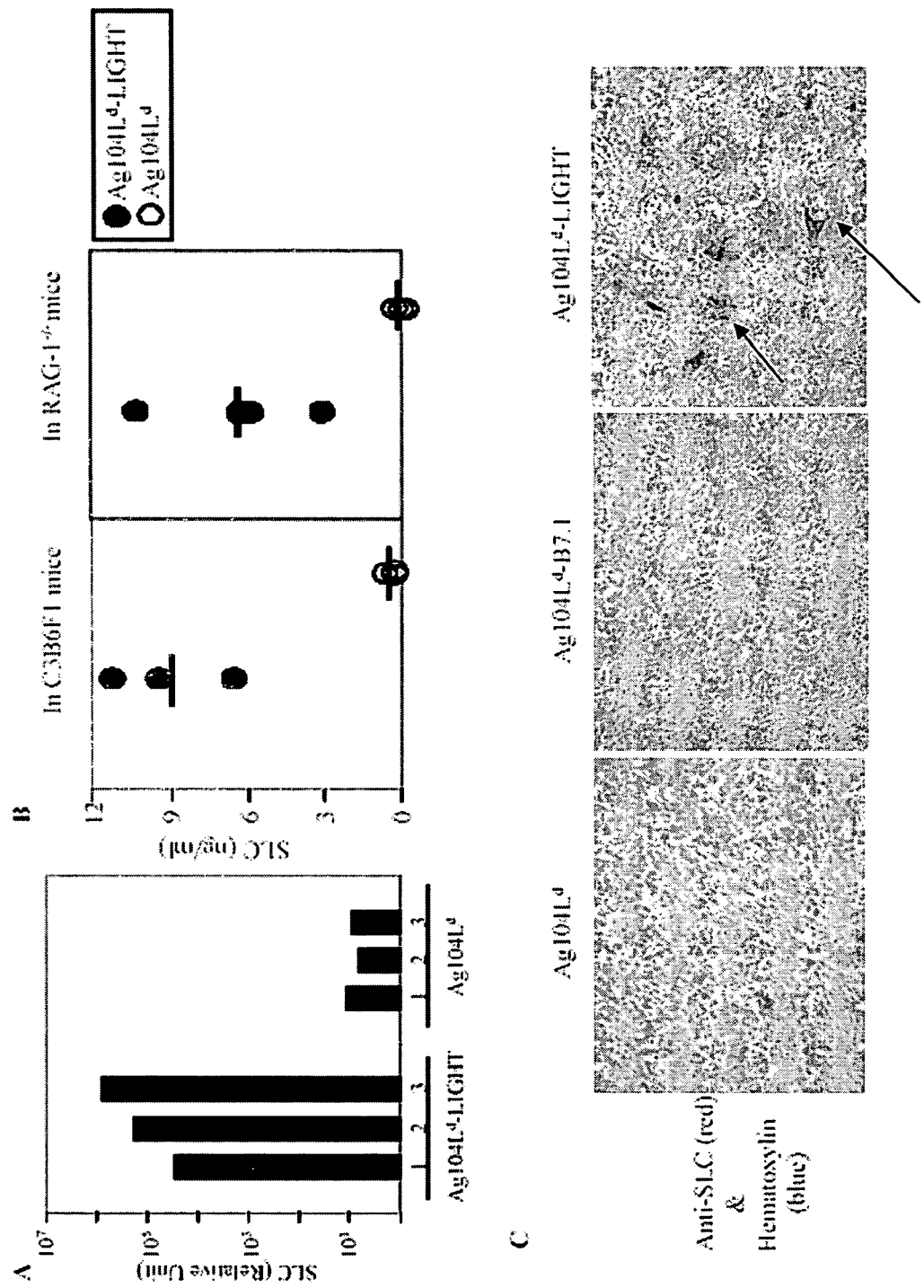
FIG. 6A-C

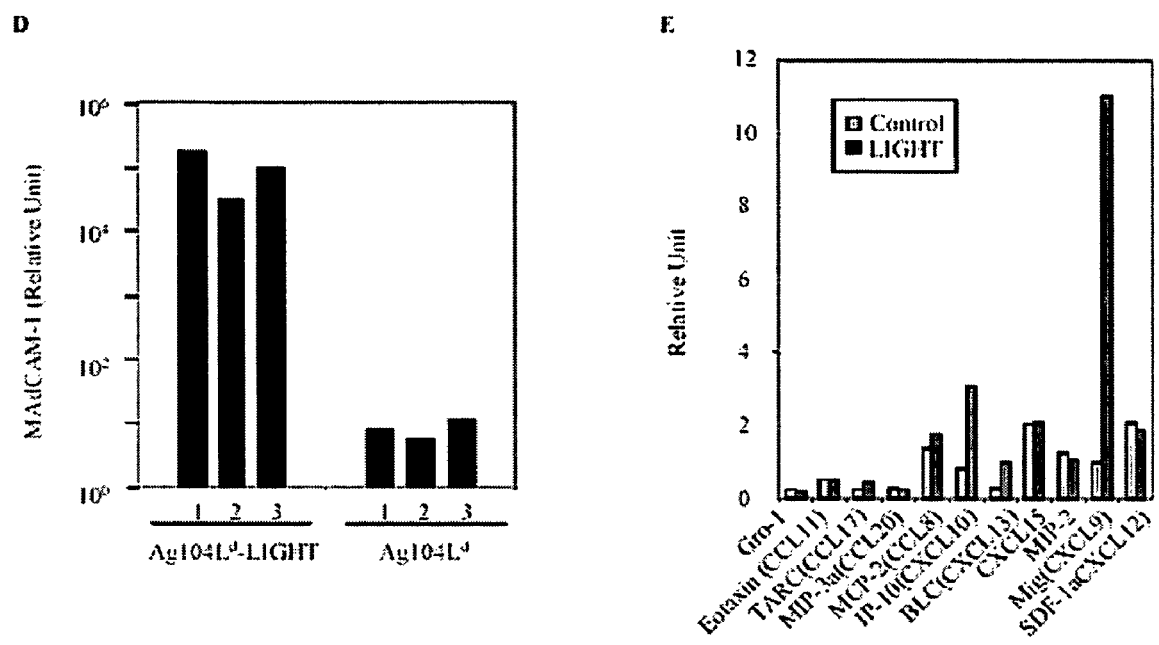
FIG. 6D-E

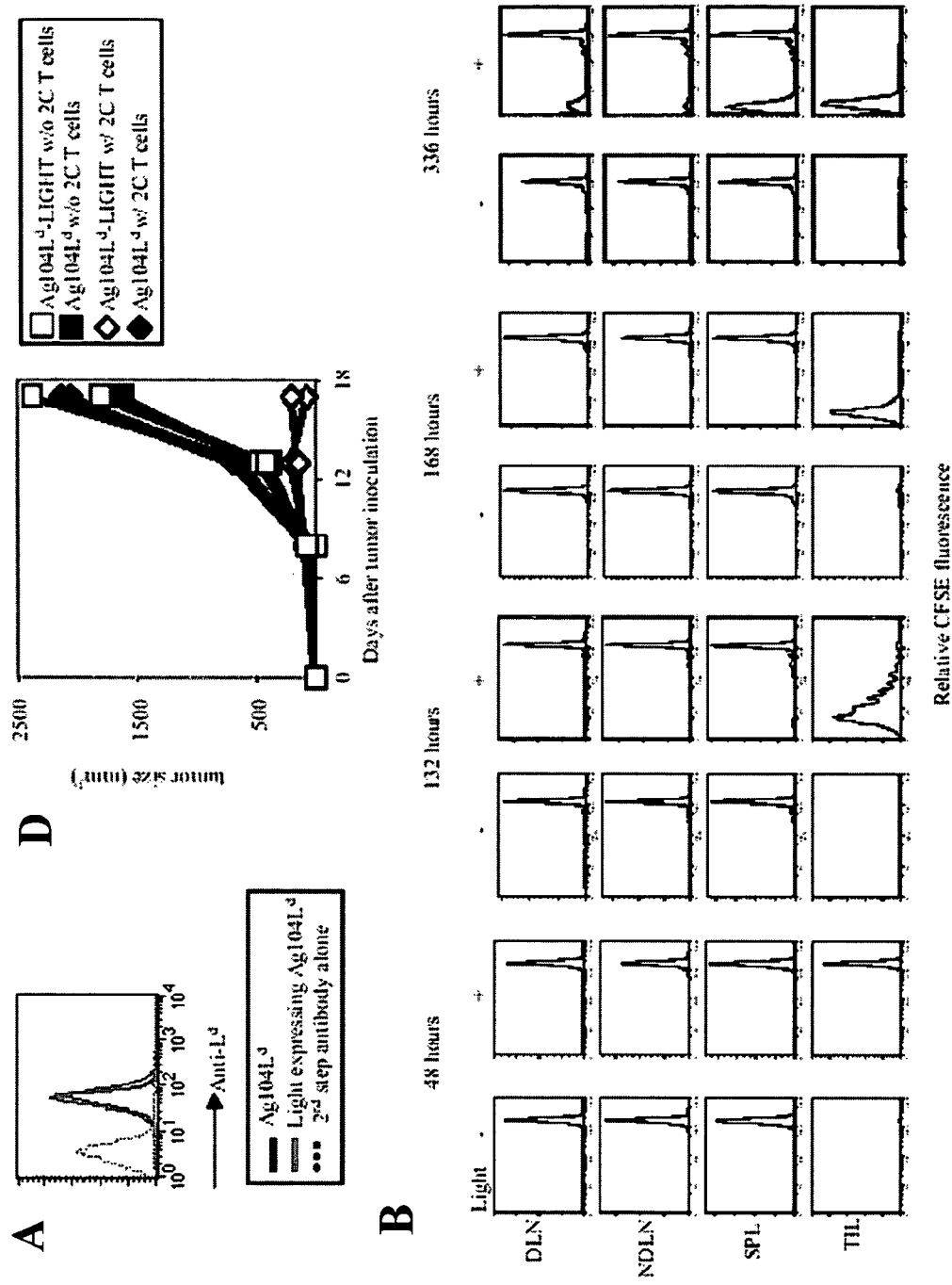
FIG. 7A-B,D gcccaacacg ctcgggcagt ttgcacagcc cgagcgtgtt gggcaattgt ggtttcctcc ggagaggagg aactcaggct tgccaaccct ttccctgggc ttcggagcct cagctgctct ggcatggaga gtgtggtaca gccttcagtg tttgtggtgg atggacagac ggacatccca ttcaggcggc tggaacagaa ccaccggaga cggcgctgtg gcactgtcca ggtcagcctg gccctggtgc tgctgctagg tgctgggctg gccactcagg gctggtttct cctgagactg catcaacgtc ttggagacat agtagctcat ctgccagatg gaggcaaagg ctcctggg<u>ag</u>

<u>aagctgatac aagatcaacg atctcaccag gccaacccag cagcacatct tacaggagcc</u> aacgccagct tgataggtat tggtggacct ctgttatggg agacacgact tggcctggcc ttcttgaggg gcttgacgta tcatgatggg gccctggtga ccatggagcc cggttactac tatgtgtact ccaaagtgca gctgagcggc gtgggctgcc cccaggggct ggccaatggc ctccccatca cccatggact atacaagcgc acatcccgct acccgaagga gttagaactg ctggtcagtc ggcggtcacc ctgtggccgg gccaacagct cccgagtctg gtgggacagc agcttcctgg gcggcgtggt acatctggag gctggggaag aggtggtggt ccgcgtgcct ggaaaccgcc tggtcagacc acgtgacggc accaggtcct atttcggagc tttcatggtc tgaaggctgc ggtgacaatg tattttgtgg agggacctct ccaggactca cctcaaaccc agcaataggg tttgaagtcc tcccttttaag gagccctgaa ctctgcagtg ctcggggcgg tgtagactgc tgacctgctt tgggcaatct tcaaatcaga gacctggaga cttggggcgt

| ggagcccagg agcgagggggt cagctcattt gcctgatatt caggaagaaa gaatcaagct

| ggggtattta tgcttctgat gcaaacactg agatttcggc tttctgggtt ttgagctgga

| ggcaagaaac cttcccagag tgtcatcagg accatgttgg caggacttgg ggctccagac

| ttgccaccac actctggcct ctcccatcca tccgctgcat tggtttccag ccaccaaaac

| agcactggcc ccctggctgc aactggccag gtacgagctt ctgagcacct acattcctca

| gggacatctt gatgagatct cagtactcag tccaatgcgc agcagcgaca gacatgccag

| gaatggttgg tcagaaggga agggaggaaa gggaggaaag aagggaatgc agaagagaag

| gggggaaaac aagaccaaaa caaaacagca acaacaaagc ggcagggagg aggtgacacc

| ctttggggata ctttagtcaa cacacttaga acagattgtg ccaggcctgt tggattcctg

| gagttgatgg gatcgtggga aggcacaatg gggagcaagt gggcttgggt tatggctcag

| tgggtaaagt gcaattatgg ggatctgagt ttgaatccct ggtacccata taaagacaca

| gatgcggtga tgggcacttg tgacaatgag atcatcaata gggaatggag acaggaggga

| cctctggggt tcactggcca ggcagtctag ctgaatcaaa gagctccaag ttcagtcgat

| agctcctgaa gatgacaact gaggctattc tccaaacccc acacgcagga cacatgcgta

| at

FIG. 9

SEQUENCE LISTING

<160> NUMBER OF SEQ ID NOS: 10

<210> SEQ ID NO 1
<211> LENGTH: 1862
<212> TYPE: DNA
<213> ORGANISM: Mus musculus

<400> SEQUENCE: 1

```
gcccaacacg ctcgggcagt ttgcacagcc cgagcgtgtt gggcaattgt ggtttcctcc      60
ggagaggagg aactcaggct tgccaaccct ttccctgggc ttcggagcct cagctgctct     120
ggcatggaga gtgtggtaca gccttcagtg tttgtggtgg atggacagac ggacatccca     180
ttcaggcggc tggaacagaa ccaccggaga cggcgctgtg gcactgtcca ggtcagcctg     240
gccctggtgc tgctgctagg tgctgggctg gccactcagg gctggtttct cctgagactg     300
catcaacgtc ttggagacat agtagctcat ctgccagatg gaggcaaagg ctcctgggag     360
aagctgatac aagatcaacg atctcaccag gccaacccag cagcacatct tacaggagcc     420
aacgccagct tgataggtat tggtggacct ctgttatggg agacacgact tggcctggcc     480
ttcttgaggg gcttgacgta tcatgatggg gccctggtga ccatggagcc cggttactac     540
tatgtgtact ccaaagtgca gctgagcggc gtgggctgcc cccaggggct ggccaatggc     600
ctccccatca cccatggact atacaagcgc acatcccgct acccgaagga gttagaactg     660
ctggtcagtc ggcggtcacc ctgtggccgg gccaacagct cccgagtctg gtgggacagc     720
agcttcctgg gcggcgtggt acatctggag gctggggaag aggtggtggt ccgcgtgcct     780
ggaaaccgcc tggtcagacc acgtgacggc accaggtcct atttcggagc tttcatggtc     840
tgaaggctgc ggtgacaatg tattttgtgg agggacctct ccaggactca cctcaaaccc     900
agcaataggg tttgaagtcc tccctttaag gagccctgaa ctctgcagtg ctcggggcgg     960
tgtagactgc tgacctgctt tgggcaatct tcaaatcaga gacctggaga cttggggcgt    1020
ggagcccagg agcgaggggt cagctcattt gcctgatatt caggaagaaa gaatcaagct    1080
ggggtattta tgcttctgat gcaaacactg agatttcggc tttctgggtt ttgagctgga    1140
ggcaagaaac cttcccagag tgtcatcagg accatgttgg caggacttgg ggctccagac    1200
ttgccaccac actctggcct ctcccatcca tccgctgcat tggtttccag ccaccaaaac    1260
agcactggcc ccctggctgc aactggccag gtacgagctt ctgagcacct acattcctca    1320
gggacatctt gatgagatct cagtactcag tccaatgcgc agcagcgaca gacatgccag    1380
gaatggttgg tcagaaggga agggaggaaa gggaggaaag aagggaatgc agaagagaag    1440
gggggaaaac aagaccaaaa caaaacagca acaacaaagc ggcagggagg aggtgacacc    1500
cttggggata ctttagtcaa cacacttaga acagattgtg ccaggcctgt tggattcctg    1560
```

-continued

```
gagttgatgg gatcgtggga aggcacaatg gggagcaagt gggcttgggt tatggctcag    1620
tgggtaaagt gcaattatgg ggatctgagt ttgaatccct ggtacccata taaagacaca    1680
gatgcggtga tgggcacttg tgacaatgag atcatcaata gggaatggag acaggaggga    1740
cctctggggt tcactggcca ggcagtctag ctgaatcaaa gagctccaag ttcagtcgat    1800
agctcctgaa gatgacaact gaggctattc tccaaacccc acacgcagga cacatgcgta    1860
at                                                                   1862
```

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
agactcagga gcccaaagca                                                 20

<210> SEQ ID NO 3
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
gttgaagcag ggcaagggt                                                  19

<210> SEQ ID NO 4
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 4
ccacctcatg ctggcctccg tc                                              22

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gacaccagct tgggcagtgt                                                 20

<210> SEQ ID NO 6
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
cagcatgccc cgtacagag                                                  19

<210> SEQ ID NO 7

```
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 7
cagaccctcc caggcagcag tatcc                                            25

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
ttcaccacca tggagaaggc                                                  20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
ggcatggact gtggtcatga                                                  20

<210> SEQ ID NO 10
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 10
tgcatcctgc accaccaact gcttag                                           26
```

INCREASED T-CELL TUMOR INFILTRATION BY MUTANT LIGHT

This application claims priority from co-pending U.S. Ser. No. 60/477,733 filed Jun. 11, 2003 and U.S. Ser. No. 60/478,126 filed Jun. 12, 2003.

The government has rights in the invention due to partial support from NIH RO1 HD 37104.

BACKGROUND OF THE DISCLOSURE

The paucity of activated T cells infiltrating established tumors in immunocompetent hosts explains the inability of hosts to dispose of tumors. Experiments in animal models as well as clinical studies indicate that the immune system can recognize and kill individual tumor cells, but a host cannot generally eradicate established solid tumors. There may be several explanations for the failure of the host to respond effectively to established tumors: 1) lack of early T cell priming due to poor direct or indirect presentation in lymphoid tissues because of an inadequate number of tumor cells (especially those of non-hemopoietic origin) migrating to the tissue; 2) inadequate numbers of immune cells migrating to tumor sites due to biological barriers around tumor tissues; 3) exhausted or short-lived activated antigen-specific T cells that fail to combat tumor growth due to limited repertoires; 4) unresponsiveness or ignorance of T cells to tumors; 5) an inhibitory microenvironment or lack of stimulation inside tumors to activate the immune system.

Clinically, increase of infiltration of T cells to the tumor site is closely associated with better prognosis. Previous studies have shown that preventive vaccinations were effective in inducing the rejection of inoculated tumor cells. After tumor growth has been established, however, the therapeutic vaccinations usually fail to reject tumor. Surgical debulk of tumor does not boost the immune response to tumors. Furthermore, it was reported that even the expression of a strong antigen on tumor cells was insufficient in promoting the rejection of an established tumor, despite the presence of excessive numbers of antigen-specific T cells in the lymphoid tissues. Lack of T cells priming and/or infiltrating an established tumor is one of the major obstacles for either natural or therapeutic approaches against antigenic cancers. In addition, insufficient expression of costimulatory molecules inside tumor tissues may fail to activate infiltrating T cells and result in the anergy of tumor-reactive T cells.

The lack of early T cell priming is possibly attributed to a few tumor cells that migrated from solid tissue to lymphoid tissues for direct presentation. Genetic analysis using bone marrow chimeras has revealed two modes of antigen presentation for priming MHC-I-restricted $CD8^+$ T cells. Direct-priming is mediated by the engagement of T cells with the cells that synthesize the protein with antigenic epitopes, whereas cross-priming is mediated by the host antigen-presenting cells that take up antigens synthesized by other cells. The mechanisms for priming tumor-specific T cells has been vigorously debated and so far remains inconclusive. Understanding how and where tumor antigens are presented to T cells would help find a therapeutic action against tumors.

Signaling via LTβR is required for the formation of organized lymphoid tissues. Lymphotoxin β receptor (LTβR) plays an important role in the formation of lymphoid structures. LTβR is activated by two members of the TNF family, membrane lymphotoxin αβ and LIGHT (FIG. 1). LTβR plays pivotal roles in the formation of LNs and the distinct organization of T, B zones in secondary lymphoid organs. Signaling via LTβR regulates the expression of chemokines and adhesion molecules within secondary lymphoid organs. Chemokines and adhesion molecules control the migration and positioning of DCs and lymphocytes in the spleen. Overexpression of soluble LT or TNF in non-lymphoid tissues was sufficient to promote functional lymphoid neogenesis.

LIGHT plays a unique role in T cell activation and the formation of lymphoid tissue. LIGHT is a ligand for LTβR and herpes virus entry mediator (HVEM). LIGHT is predominantly expressed on lymphoid tissues. Interactions between LIGHT and LTβR restore lymphoid structures in the spleen of $LT\alpha^{-/-}$ mice. In addition, upregulation of LIGHT causes T cell activation and migration into non-lymphoid tissues and forms lymphoid-like structures. Conversely, $LIGHT^{-/-}$ mice showed impaired T cell activation and delayed cardiac rejection. Therefore, LIGHT is a potent costimulatory molecule that also promotes the formation of lymphoid tissues to enhance local immune responses.

Lack of efficient priming of naïve T cells in draining lymphoid tissues and inability to expand tumor-specific T cells within tumors prevent the eradication of cancer.

SUMMARY OF THE INVENTION

Mutant LIGHT creates a lymphoid-like microenvironment that expresses chemokines, adhesion molecules and co-stimulatory molecules for priming T-cells to kill tumor cells.

Mutant LIGHT ($LIGHT^m$) is generated to prevent protease digestion so LIGHT can be expressed on tumor cells. Non-mutant LIGHT is not expressed on the surface of tumors and does not induce effective anti-tumor activity.

The introduction of mutant $LIGHT^m$, a ligand for stroma expressed lymphotoxin receptor and T cell expressed HVEM, inside the tumor environment elicited high level of chemokines and adhesion molecules, accompanied by massive infiltration of naïve T lymphocytes. Mutant light (designated $LIGHT^m$), has the proteolytic site EKLI from positions 79-82 deleted from the amino acid sequence of normal LIGHT (FIG. 3A) (Tamada et al., 2000). LIGHT enhances rejection of an established, highly progressive parental tumor at local and distal sites. $LIGHT^m$-expressing tumor cells are the basis for a clinically relevant therapeutic and prophylactic vaccines to eradicate well-established parental tumors and prevent new tumors forming through metastasis.

$LIGHT^m$-expressing tumors as a therapeutic vaccine attracts more naïve T cells and then activates them so that more anti-tumor specific T cells are generated to combat local and distal tumors.

$LIGHT^m$ and tumor (or tumor antigens) prime T cells and lead to long-term protection as a preventive vaccine.

A novel method to treat tumors (solid tumors in particular) is to create lymphoid-like microenvironments that express chemokines, adhesion molecules, and costimulatory molecules required for priming naïve T cells and expanding activated T cells by the use of mutant LIGHT molecules. Broader T cells are generated against tumors. Adenoviral vectors that include mutant LIGHT encoding sequences, are effective against tumors and metastasis. Tumor volume was reduced in vivo when vectors delivered mutant LIGHT to tumors as compared to tumors injected with control vectors.

BRIEF DESCRIPTION OF THE DRAWINGS

FIG. 6A. illustrates increased LTβR-associated chemokines and adhesion molecules in Ag104L$^d$-LIGHT$^m$ tumors. (1) $5 \times 10^6$ Ag104L$^d$, (2) Ag104L$^d$-B7.1 or (3) Ag104L$^d$-LIGHT$^m$ tumor cells were inoculated subcutaneously into C3B6F1 or B6/RAG-1$^{-/-}$ mice. Tumor tissues were collected 10-14 days post tumor challenge. B. The same amount of tumor tissue was thoroughly ground in the PBS containing protease inhibitors. SLC in the supernatant was measured by ELISA after centrifugation. Ag104L$^d$-LIGHT$^m$ tumors collected from both C3B6F1 mice and B6/RAG-1$^{-/-}$ mice, as indicated, contained higher level of SLC than the parental tumors. C. Tumor tissues from Ag104L$^d$, Ag104L$^d$-B7.1 or Ag104L$^d$-LIGHT$^m$ were fixed in 10% neutral formalin, sectioned and stained with anti-murine SLC followed by second step antibody, color development (red) is shown by arrows; background was hemotoxilyn counter-stained (blue). D. Total RNA was isolated from the tumor tissue and real-time quantitative RT-PCR was performed to analyze the expression of adhesion molecule MAdCAM-1 and chemokine SLC. E. Gene array was performed to analyze the expression of other chemokines as indicated in the LIGHT$^m$-expressing Ag104L$^d$ and parental tumor using total RNA purified from the tumor tissue. The increase of LTβR-associated chemokines and adhesion molecules was found in the LIGHT$^m$-expressing tumor tissues. Relative expression levels were shown in the left panel. Fold of increase of expression by Ag104L$^d$-LIGHT$^m$ was shown in the right panel. Total RNA was isolated from the tumor tissue and gene array was performed to analyze the expression of chemokines as indicated in the LIGHT$^m$-expressing Ag104L$^d$ and parental tumor.

FIG. 9 shows the nucleic acid sequence (SEQ ID NO: 1) that encodes a LIGHT protein. The start codon ATG is indicated in bold and the region encoding a proteolytic site that has been deleted in LIGHT$^m$ is underlined.

DETAILED DESCRIPTION OF THE INVENTION

Expression of LIGHT$^m$ on tumor cells promotes tumor rejection. The tumor Ag104A and its derivatives were used as one of tumor models. Ag104A was originally derived from spontaneous osteosarcoma in C3H (H-2$^k$) mice and even very low dose of Ag104A (10$^4$) can grow aggressively in C3H or B6C3F1 mice with very little infilatrates. When strong antigen, L$^d$, was introduced into a tumor, the tumor remained resistant to immune recognition, suggesting a possible strong tumor barrier. Ag104L$^d$ tumor transfected retrovirally with mutated LIGHT$^m$ stably expresses LIGHT$^m$ on its surface.

LIGHT$^m$-Ag104L$^d$ tumor was first inoculated into B6C3F1 mice for 2 weeks, then 1×10$^6$ 2C T cells were transferred into the established tumor bearing mice. Impressively, all established LIGHT$^m$-Ag104L$^d$ tumors (10/10) were rejected one week after the transfer of 2C T cells while no Ag104L$^d$ tumors (0/10) were rejected. Even though B7-1 is a strong costimulatory molecule for inducing T cell activation and expansion, in contrast to LIGHT$^m$, expression of B7-1 on Ag104L$^d$ was not sufficient for the rejection of a tumor. These data suggest that LIGHT$^m$ may be more potent than B7-1 to break tumor tolerance. Considering the dual effect of LIGHT$^m$, local expression of LIGHT$^m$ at the tumor site may attract dendritic cells and T cells across the tumor "barrier" by regulating the expression of lymphoid tissue chemokines and adhesion molecules. Furthermore, local expression of LIGHT$^m$ becomes a strong costimulatory molecule that may enhance direct presentation of tumor antigens to antigen-specific T cells and prevent the anergy of infiltrated T cells within the tumor microenvironment. H-2$^b$ background tumors, MC57 tumors (fibrosarcoma), MC57-L$^d$ and MC57-SIY with or without LIGHT$^m$ expression have been generated and are used in B6 mouse models, including LTβR, LIGHT$^m$, and HVEM KO mice to further characterize the role of LIGHT$^m$ and its receptors in tumor immunity. LIGHT$^m$ appears to have multiple functions in mediating tumor immunity. LIGHT$^m$ also may enhance tumor apoptosis in vivo. Interestingly, intratumoral injection of cDNA encoding LIGHT$^m$ induced an antigen-specific cytolytic T-cell response and therapeutic immunity against the established murine tumor P815.

Figure 1:
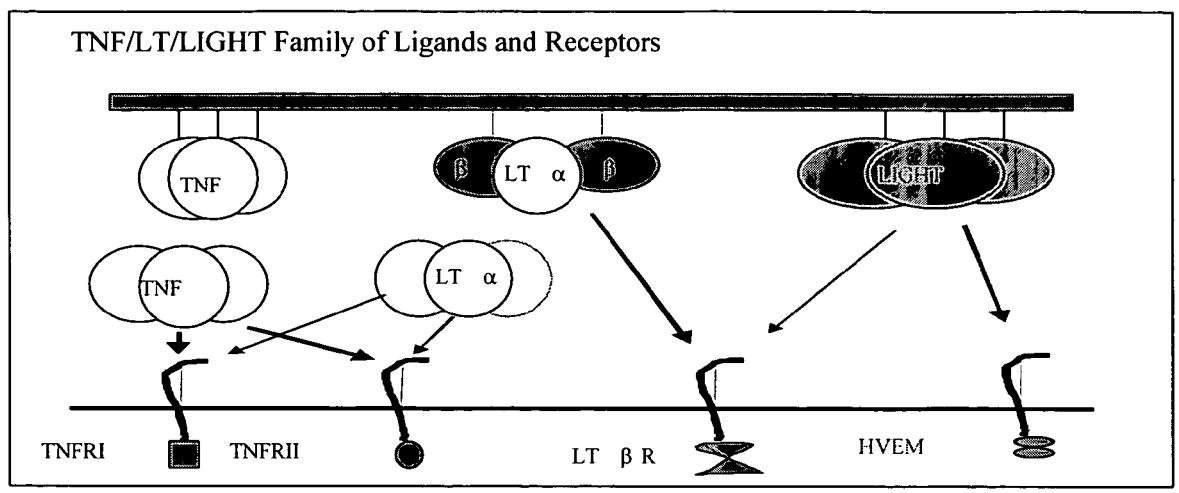
FIG. 1 illustrates a current model for the interactions between TNF/LT/LIGHT family members. LTβR binds to both membrane LT and LIGHT, while HVEM binds to LIGHT. Soluble TNF3 and LTα3 bind to TNFRI and TNFRII.
Figure 2:
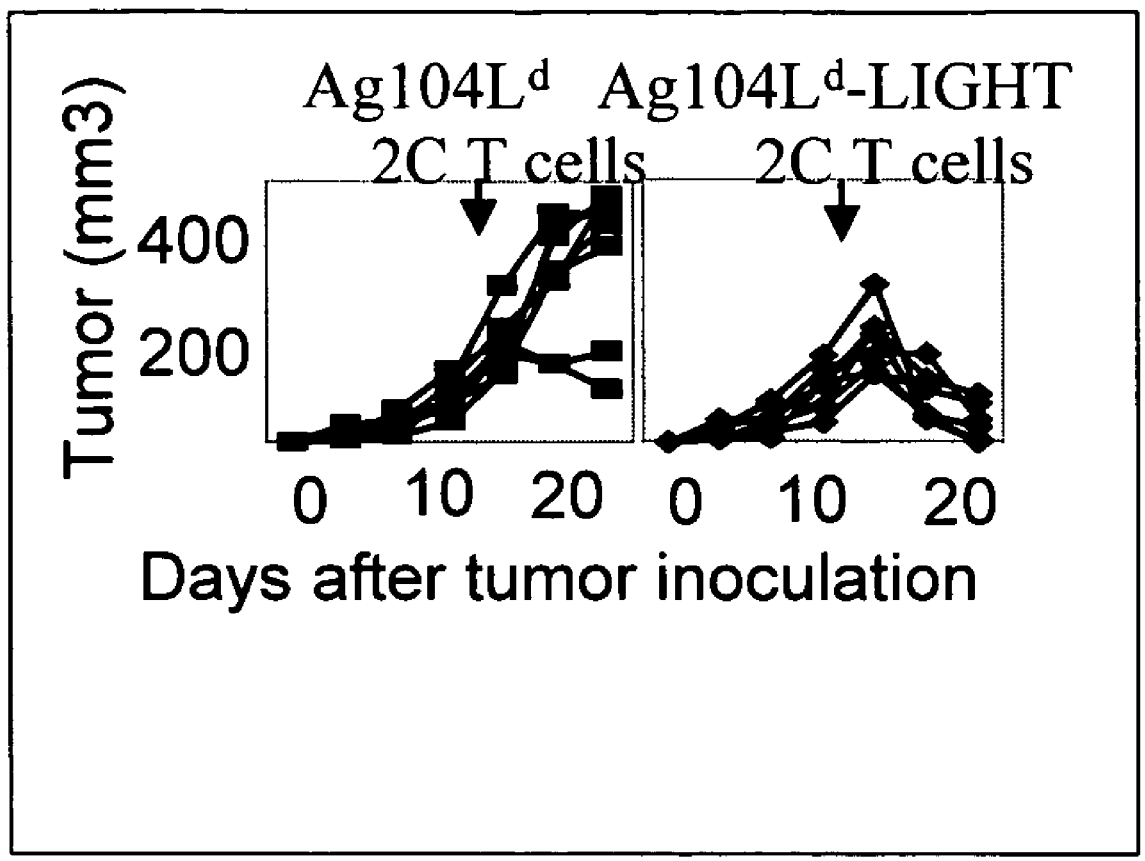
FIG. 2 shows that both LIGHT$^m$ and antigen specific T cells are required for optimal tumor rejection. Tumor cells ($5 \times 10^5$) were inoculated into CB6F1: Tumor transfected with LIGHT$^m$ on the left side and control tumor on the right side. Fourteen days later, 2C T cells ($10 \times 10^5$) were transferred into the mice and tumor growth was monitored. Tumor growth curves are shown.
Figure 3:
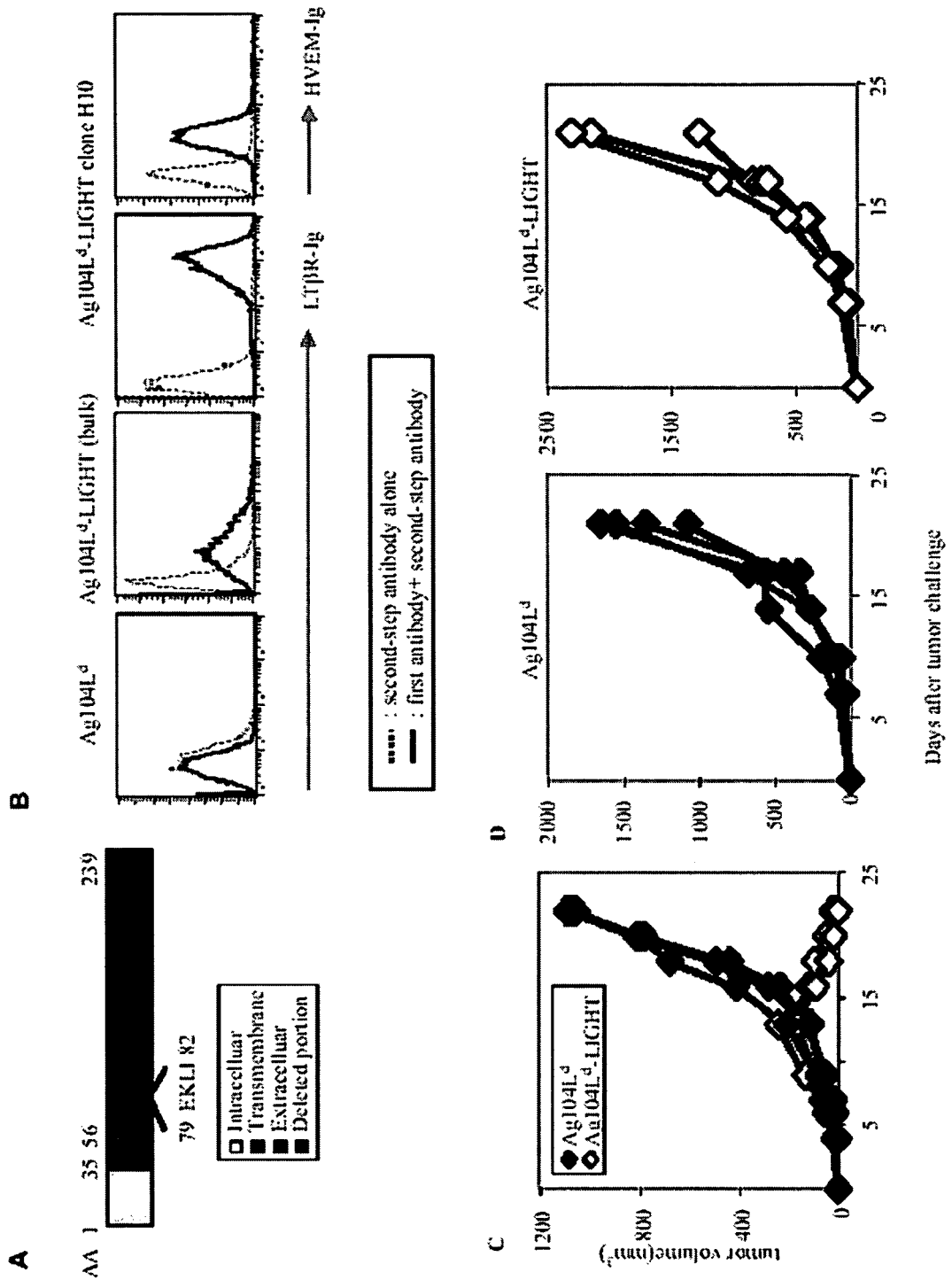
FIG. 3 shows the growth kinetics of LIGHT-expressing Ag104L$^d$ and parental tumor in C3B6F1 and B6/RAG-1$^{-/-}$ mice. A. Four amino acids corresponding to a proteolytic site were deleted from the extracellular domain of LIGHT to ensure stable expression on the surface of tumor cells. B. Ag104L$^d$ parental tumor cells, Ag104L$^d$ tumor cells transfected with LIGHT$^m$, as bulk or cloned, were stained with LTβR-human Ig, HVEM-murine Ig, followed by FITC-conjugated donkey antibody against human IgG or goat antibody against murine IgG, respectively (solid lines). Tumor cells stained with second-step antibody alone were shown in dotted lines. C. C3B6F1 mice were inoculated subcutaneously with $5 \times 10^6$ Ag104L$^d$ parental tumor cells (solid diamonds) or LIGHT$^m$-expressing Ag104L$^d$ tumor cells (open diamonds). Ag104L$^d$ grew progressively while Ag104L$^d$-LIGHT$^m$ was rejected in C3B6F1 mice. D. B6/RAG-1$^{-/-}$ mice were challenged with subcutaneous injection of $10^6$ Ag104L$^d$ tumor cells (solid diamonds) or LIGHT$^m$-expressing Ag104L$^d$ tumor cells (open diamonds). Both tumors grew progressively in the B6/RAG-1$^{-/-}$ mice.

LIGHT$^m$ expressed inside the tumor augmented host resistance more than 500 times. Fibrosarcoma Ag104L$^d$ was highly tumorigenic and grew out 100% when 10$^4$ cells were injected into recipient mice C3B6F1 subcutaneously (Table 1). It has been reported that 2C T cell receptor (TCR) transgenic mice, which were filled with T cells against antigen L$^d$ expressed on the tumor, failed to eradicate it even after rejection of skin graft containing the same antigen (Hans, 1997). How to direct tumor-specific T cells into the tumor and activate them at the tumor sites seems to be one critical hurdle for rejection, as well as immunotherapy of cancer clinically. LIGHT expressed in the tumor environment may break the tolerance by attracting and activating T cells inside the tumor via LTβR and HVEM, respectively, leading to tumor rejection (FIG. 2). To demonstrate this, LIGHT was expressed on this tumor cell line by retroviral transduction utilizing retroviral vector MFG. Initially, LIGHT expression was not detected on the tumor cell surface after transduction. Because LIGHT has proteolytic sites in its sequence, which may prevent its stable presence on the surface of a tumor cell line, a mutant version of LIGHT (LIGHT$^m$), which reduces proteolysis of LIGHT on the membrane was used. (FIG. 3A). After retroviral transduction of mutant LIGHT$^m$/MFG to AG104L$^d$, LIGHT$^m$ expression was detected on the surface of transduced tumor cells by LTβR-Ig. (FIG. 3B). These cells were defined as Ag104L$^d$-LIGHT$^m$ bulk. LIGHT$^m$-expressing Ag104L$^d$ tumor cells were further cloned by limiting dilution. One of the clones, H10 was used in the most of the experiments unless specified otherwise. Mutant LIGHT$^m$ was able to bind both of its receptors, LTβR and HVEM. Ag104L$^d$-LIGHT$^m$ bulk and all the clones tested bound receptors of LIGHT$^m$, LTβR and HVEM, shown by their ability to be stained by soluble LTβR and HVEM. The typical staining profile of Ag104L$^d$-LIGHT$^m$ bulk and clone H10 by LTβR-Ig and HVEM-Ig was shown (FIG. 3B). The growth of parental tumor cells and LIGHT-transfectants was the same in both tissue culture and RAG-1$^{-/-}$ mice (FIG. 3D). Different number of LIGHT$^m$-expressing tumor cells, bulk or clone H10, were inoculated subcutaneously to C3B6F1 mice. The recipients rejected the highest dose of LIGHT$^m$-expressing tumor cells injected, 5×10$^6$, which was 500 times of the dose at which the parental tumors grew progressively 100% (Table 1). The typical growth kinetics of the LIGHT$^m$-expressing tumor, bulk or clone H10, and the parental one when 5×10$^6$ cells were inoculated was shown in FIG. 3C. Ag104L$^d$-LIGHT$^m$ grew in the first two weeks after inoculation followed by subsequent regression when parental tumor continues to progress and kill the host in 3-4 weeks (FIG. 3C). The tumor rejection is likely to be LIGHT$^m$-dependent since the LIGHT$^m$-expressing tumors grew if LIGHT$^m$ function was blocked with soluble LTβR (Table 1). The tumor rejection is dependent on lymphocytes. LIGHT$^m$-expressing Ag104L$^d$ grew equally progressive as the parental tumor in RAG-1$^{-/-}$ mice, which lacked lymphocytes (FIG. 3D). CD8$^+$ T cells but not CD4$^+$ T cells were essential to mediate the rejection of the LIGHT-expressing Ag104L$^d$ because C3B6F1 mice, which were depleted of CD8$^+$ T cells with anti-CD8 antibody, failed to reject these tumors (Table 1). However, CD4$^+$ T cells are not required for the tumor rejection.

Figure 5:
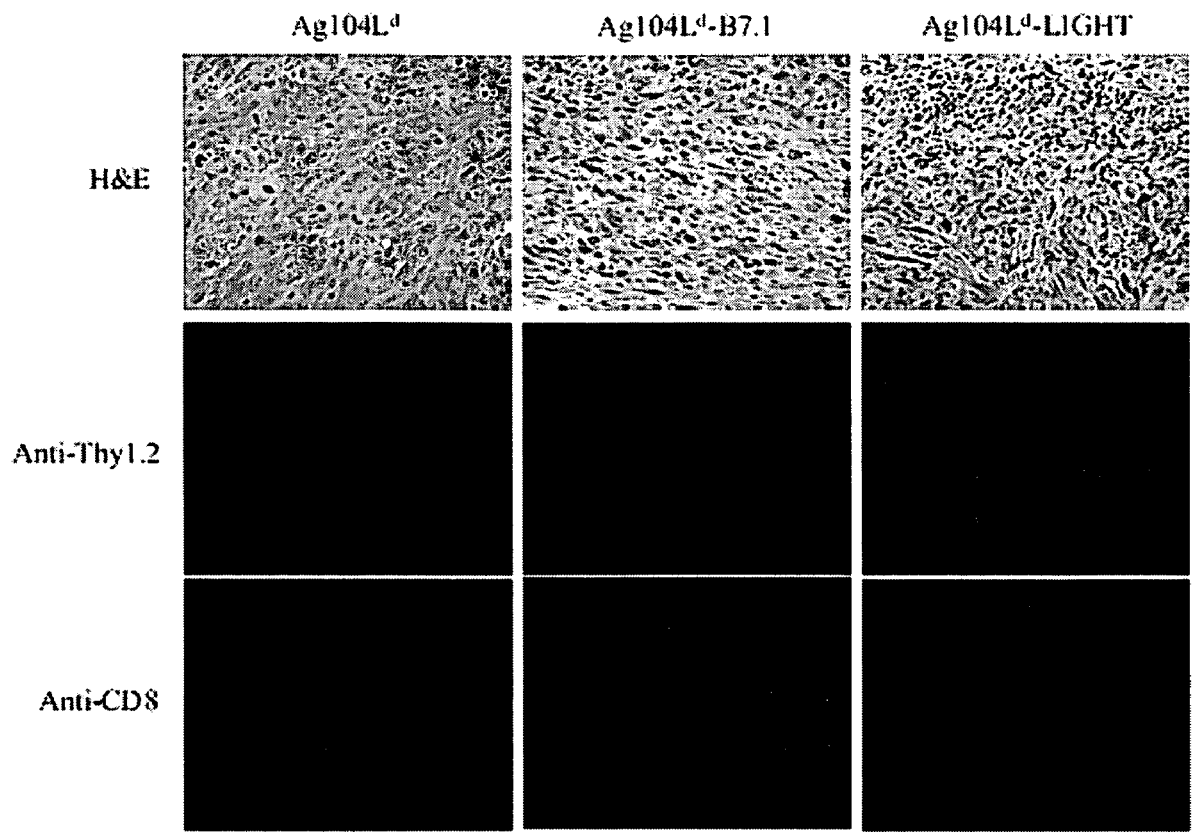
FIG. 5 are photographic illustrations showing increased infiltration of CD8$^+$ T cells in LIGHT$^m$-expressing Ag104L$^d$ tumor tissues. $5 \times 10^6$ Ag104L$^d$, Ag104L$^d$-B7.1 or Ag104L$^d$-LIGHT$^m$ tumor cells were injected subcutaneously to C3B6F1 mice. Tumor tissues were collected 10-14 days after tumor inoculation. Frozen sections of tumor tissues were stained with HE (upper panel) or anti-Th1.2-PE (middle panel), anti-CD8-PE, as indicated (lower panel).

LIGHT$^m$-mediated tumor environment has more infiltrating CD8$^+$ T cells. To investigate the possible mechanisms underlying LIGHT$^m$-mediated tumor rejection, 5×10$^6$ LIGHT$^m$-expressing Ag104L$^d$ or the same number of parental tumor cells were injected subcutaneously to the C3B6F1 mice. Ten to fourteen days after tumor inoculation, before LIGHT$^m$-expressing tumors were rejected, tumor tissues were collected. HE-staining of the tumor tissues showed large amount of infiltrating lymphocytes (FIG. 5) while the parental tumors showed very little infiltration (FIG. 5). Immunofluorescent staining confirmed that among the infiltrating lymphocytes, large amount of Thy1.2$^+$ T cells (FIG. 5), especially CD8$^+$ T cells were present inside LIGHT$^m$-expressing tumors (FIG. 5).

Figure 4:
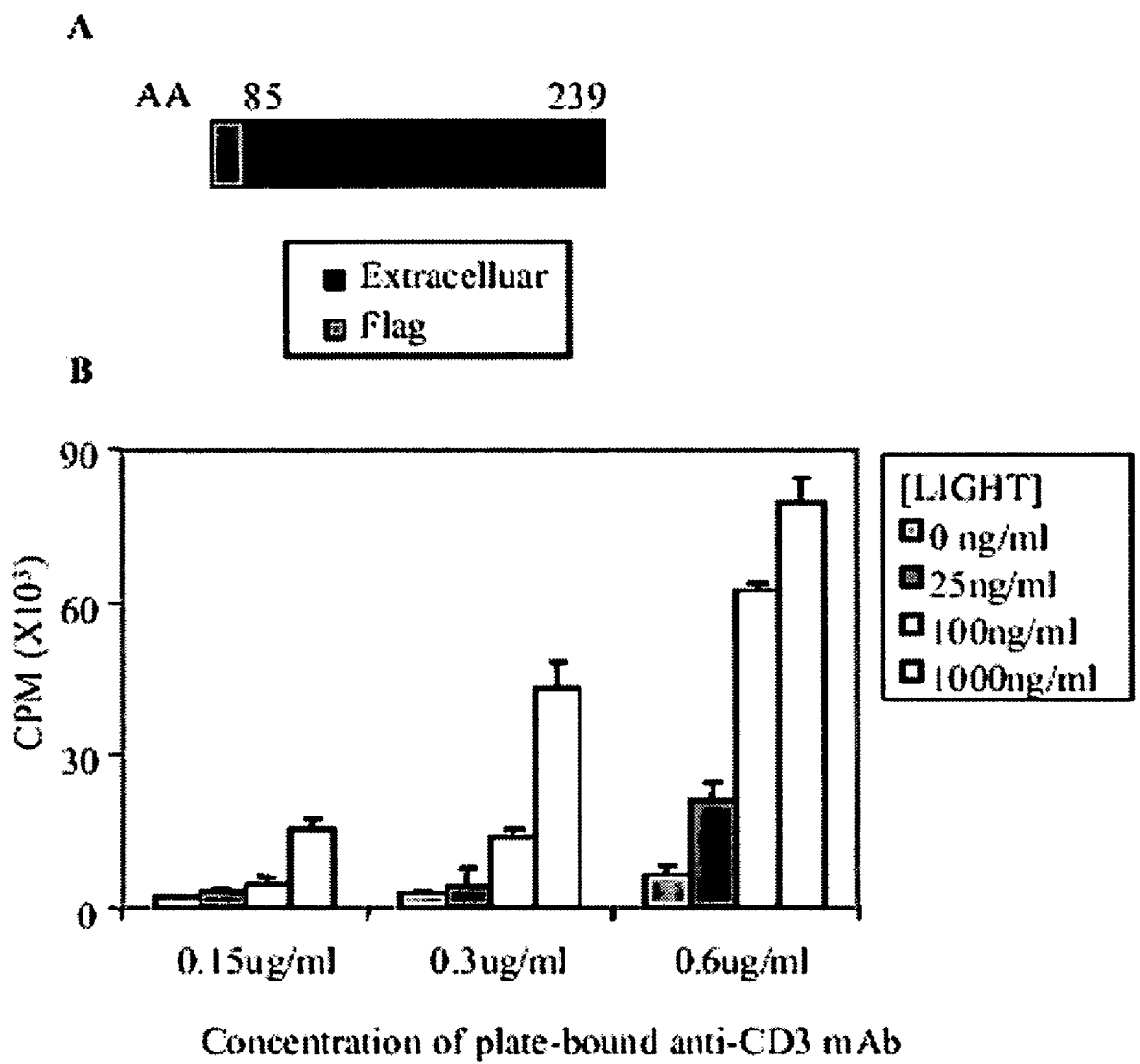
FIG. 4 shows that a modified extracellular domain of LIGHT$^m$ is sufficient to co-stimulate purified T cell responses. A. Recombinant protein containing extracellular domain of LIGHT$^m$ (85-239 amino acids) and a flag sequence to facilitate purification of recombinant protein. B. Purified T cells were stimulated with immobilized extracellular domain of LIGHT$^m$ in the presence of antibody against CD3 (anti-CD3).

Modified extracellular domain of LIGHT is sufficient to co-stimulate T cells It has been reported that LIGHT has potent co-stimulatory activity leading to T cell proliferation. In mutant form of LIGHT, four amino acids corresponding to a proteolytic site in the extracellular domain, very close to transmembrane domain of the molecule were deleted (FIG. 3A). The mutation in the LIGHT$^m$ molecule affects its co-stimulatory effect. Recombinant LIGHT$^m$ protein was made that only contains amino acids 85 to 239, a shortened form of extracellular domain, with a flag peptide to facilitate purification (recombinant LIGHT$^m$) (FIG. 4A). The modified extracellular domain of LIGHT$^m$ was sufficient to co-stimulate T cells. For this test, an in vitro co-stimulation assay with plate-bound recombinant LIGHT$^m$ was used to stimulate purified mouse T cells in the presence of an immobilized monoclonal antibody against CD3 at a sub-optimal dose. Immobilized recombinant LIGHT$^m$ strongly stimulated a proliferation of purified mouse T cells in a dose-dependent manner in the presence of sub-optimal amounts of antibody against CD3 (FIG. 4B). The modified extracellular domain of LIGHT$^m$, which is amino acid 85 to 239 excluding the proteolytic site deleted from the LIGHT$^m$ molecule, is sufficient to co-stimulate T-cell growth when engagement of the T-cell receptor occurs.

Tumor expressing B7.1 molecule contains comparable infiltrating T cells to parental tumor. Infiltrating CD8$^+$ T cells correlated with tumor rejection by LIGHT$^m$-mediated tumor environment. Because LIGHT$^m$ has potent co-stimulatory effect on T cells, a question was whether B7.1, another potent co-stimulatory molecule is sufficient to mediate tumor rejection associated with large number of infiltrating T cells. $5 \times 10^6$ Ag104L$^d$-B7.1 tumor cells, which were transduced the same way as Ag104L$^d$-LIGHT$^m$, were inoculated to C3B6F1 mice subcutaneously. These tumors grew progressively in the recipients. HE-staining on the tumor tissues showed little lymphocyte infiltration (FIG. 5). Immunofluoresent staining with anti-Thy1.2 and anti-CD8 revealed that Ag104L$^d$-B7.1 tumor tissues contained comparable level of T cells including CD8$^+$ T cells infiltration with parental tumor Ag104L$^d$ (FIG. 5), which was substantially less comparing with LIGHT$^m$-expressing Ag104L$^d$ (FIG. 5). This data was consistent with previous findings that Ag104L$^d$ expressing two co-stimulatory molecules, B7.1 and CD48, failed to be rejected by 2C TCR transgenic mice (Hans, 1997 JEM). These lines of evidence suggested that strong co-stimulation alone is not sufficient to mediate tumor rejection in these tumor models.

LIGHT$^m$-mediated tumor environment contains high level of chemokine SLC and up-regulated adhesion molecule MAdCAM-1. A question was, what is unique about a LIGHT-mediated tumor environment? Although LIGHT$^m$ binds to HVEM, the receptor expressed on T cells, via which LIGHT$^m$ likely mediates its co-stimulation of T cells, LTβR is another receptor interacting with LIGHT$^m$. LTβR signaling is an important regulator for chemokine SLC and adhesion molecule MAdCAM-1, which controls the homing of naïve T cells to the secondary lymphoid tissues. LIGHT$^m$ in the tumor environment could interact with LTβR on these tumor stromal cells to up-regulate SLC and MAdCAM-1 in the tumor environment. Tumor tissue was collected from either parental Ag104L$^d$ or LIGHT$^m$-expressing Ag104L$^d$ 10-14 days after inoculation. Real time RT-PCR, showed that LIGHT$^m$-positive tumor mass expressed higher level of SLC than parental tumor (FIG. 6A). This result was independently confirmed by ELISA detecting abundance of SLC in Ag104L$^d$-LIGHT$^m$ (FIG. 6B). SLC was barely detectable in the parental tumors (FIG. 6B). To exclude the possibility that the higher SLC detected in the LIGHT$^m$-expressing tumor was solely due to more vigorous ongoing immune responses with more T cells in the tumor environment, tumor tissues from RAG-1$^{-/-}$ tumor bearers. Ag104L$^d$-LIGHT$^m$ tumors growing in the lymphocyte deficient mice contained higher level of SLC than parental tumors (FIG. 6B). Furthermore, equal growth of both LIGHT$^m$-positive and negative tumors in RAG-1$^{-/-}$ mice suggested that chemokine SLC alone is not sufficient to mediate tumor rejection. These data were consistent with the immunohistochemical staining of tissue sections from other 5 pairs of LIGHT$^m$-positive and negative tumor samples collected from C3B6F1 tumor bearing animals (TBA). Very strong staining of SLC was detected near stroma-rich area in the LIGHT-expressing tumors surrounded by high density of infiltrating lymphocytes, as clearly shown by SLC and hemotoxylin double-stained tumor tissues (FIG. 6C). However, SLC was not detected in the stroma-rich area on the tumor tissues that are negative for LIGHT$^m$ (FIG. 6C). The tissues from B7.1-expressing tumors also had no SLC staining and very few lymphocytes infiltration, similar to those of control tumors (FIG. 6C).

Adhesion molecules are critical for the migration of lymphocytes into the peripheral tissues and LTβR signaling is important for the expression of one of the adhesion molecules MAdCAM-1 (Kang, 2002). The expression level of MAdCAM-1 in the LIGHT$^m$-expressing tumor mass or the parental tumor was checked by real-time RT-PCR. Increased expression for adhesion molecule MAdCAM-1 in the LIGHT$^m$-expressing tumor mass compared to parental ones (FIG. 6D). These experiments strongly suggested that LIGHT in the tumor environment interacts with LTβR derived from tumor stroma to up-regulate chemokine SLC and adhesion molecule MAdCAM-1 to attract lymphocytes into the tumor environment.

In addition to lymphoid tissue chemokines, LTβR signaling also regulates a set of INF-γ-induced chemokines IP-10 and Mig. A gene array to compare the expression level of other chemokines revealed that IP-10 and Mig, which can potentially attract activated T cells, also were specifically up-regulated in the LIGHT$^m$-mediated tumor environment compared with parental one while other chemokines tested were comparable between LIGHT$^m$-positive or negative tumors. Therefore, LIGHT$^m$ plays an important role in the formation of lymphoid microenvironment for recruiting naïve and possibly activated, T cells.

Naïve T cells can be recruited into LIGHT$^m$-mediated tumor environment where they proliferate and reject tumors. LIGHT$^m$-mediated tumor environment contains high level of chemokine SLC and adhesion molecule MAdCAM-1, which potentially allow entry of naïve T cells. Three questions addressed directly were: 1) whether such environment is able to recruit naïve T cells; 2) whether naïve T cells can be activated inside the tumor, in vivo, in the presence of LIGHT$^m$; and 3) whether tumor bearing the antigen can be rejected by these T cells. The antigen L$^d$ expressed by Ag104, is an allogeneic MHC class I molecule that presents peptides derived from the house-keeping gene α-ketoglutarate dehydrogenase, on the surface of the tumor cells. In C3B6F1 (H-2$^{kXb}$) or B6 (H-2$^k$) hosts, adoptively transferred 2C TCR transgenic T cells only recognize Ag104 tumor cells directly presenting L$^d$ because 2C T cell responses required L$^d$ in its naïve form, which is lost when the antigen is processed and cross-presented by antigen presenting cells (APCs) from the hosts. Subcutaneously growing tumors are very inefficient to prime T cells via direct pathway in the lymphoid tissues. Ag104L$^d$ inoculated subcutaneously 24 hours after $3-5 \times 10^5$ CFSE-labeled 2C T cells were adoptively transferred into the C3B6F1 hosts. Proliferation of 2C T cells was not detected or measured by fluorescent dye CFSE dilution in the tumor draining lymph nodes, other non-draining lymph nodes or spleen up to 7 days after Ag104L$^d$ tumor challenge. 2C T cells in the secondary lymphoid organs maintained their naïve phenotype as indicated by low CD25, CD69 or CD44 on their surface during the 7-day observation. These indicated that T cells specific for antigens expressed on the tumor cells could not be activated if the antigens could not be cross-presented efficiently for many reasons. Consequently, $10^6$ Ag104L$^d$ tumor cells were not rejected by C3B6F1 mice even when as many as 5×10$^6$ tumor antigen specific 2C T cells were transferred into the hosts.

Figure 7C:
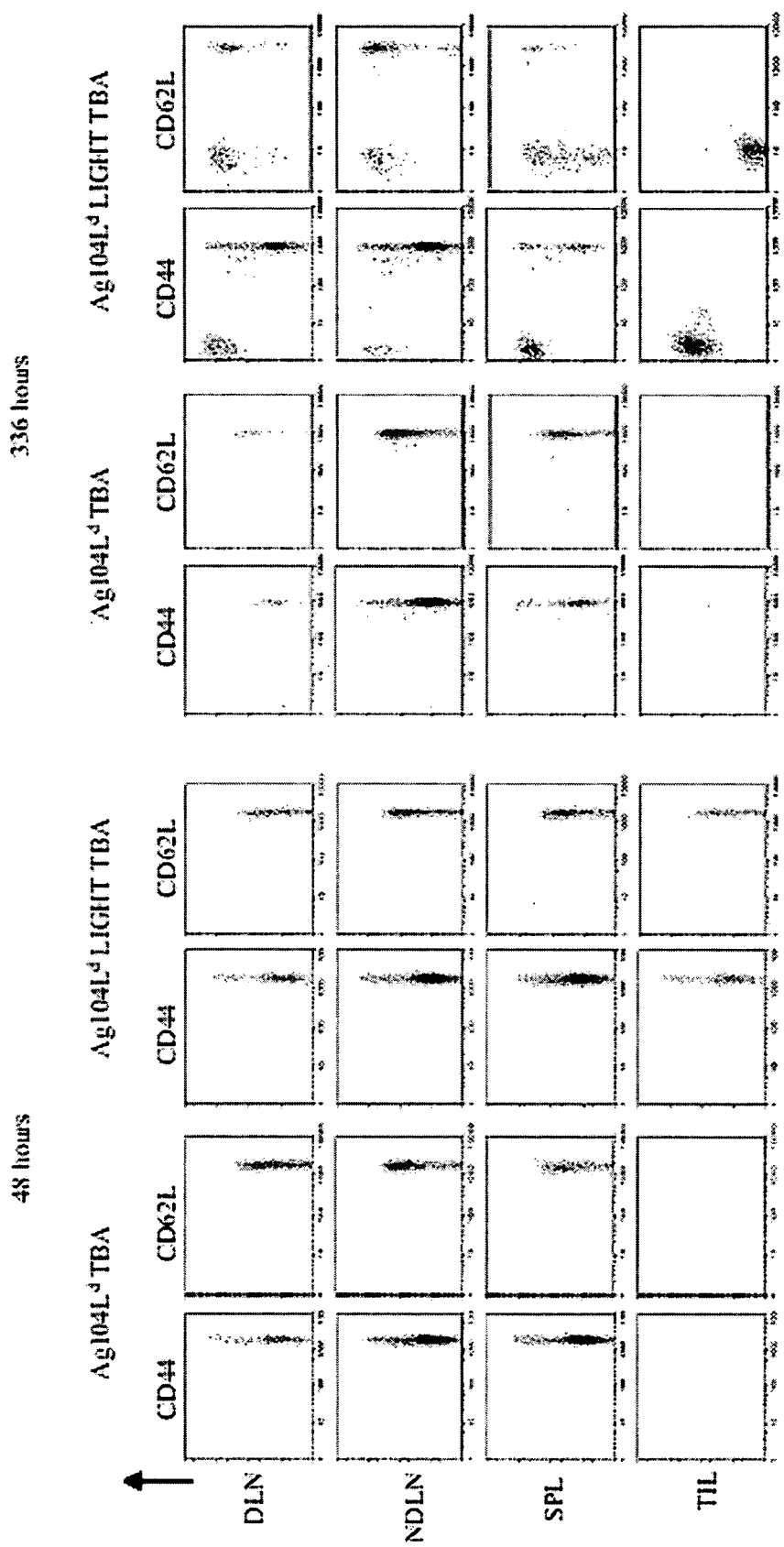
FIG. 7 shows that LIGHT$^m$-mediated Ag104L$^d$ tumor environment recruits naïve 2C T cells, activates them and causes tumor rejection. A. Ag104L$^d$ and Ag104L$^d$-LIGHT$^m$ expressed the same level of antigen L$^d$. Ag104L$^d$ (black solid line) or Ag104L$^d$-LIGHT$^m$ (gray solid line) tumor cells were stained with anti-L$^d$ followed by second step staining of FITC-conjugated goat antibody against murine IgG. Tumor cells stained with second-step antibody alone were shown in dotted lines. B. OT-1/RAG-1$^{-/-}$ mice were injected with $10^6$ Ag104L$^d$ or Ag104L$^d$-LIGHT$^m$ tumor cells subcutaneously. $3 \times 10^6$ CFSE-labeled 2C TCR transgenic T cells were transferred to these mice 10-14 days after tumor challenge. Tumor draining lymph nodes, non-draining lymph nodes, spleen and tumor tissue were collected 48, 132, 168 and 336 hours, as indicated, after 2C T cell transfer. T cells infiltrating tumors were isolated by a positive-selecting magnetic column. Cells from lymph nodes, spleen and tumor were subjected to FACS analysis after stained with anti-CD8 and 2C TCR clonotypic antibody 1B2. Proliferation of CD8 and 1B2 double positive 2C T cells was shown. C. OT-1/RAG-1$^{-/-}$ mice were injected with $10^6$ Ag104L$^d$ or Ag104L$^d$-LIGHT$^m$ tumor cells subcutaneously. $3 \times 10^6$ CFSE-labeled 2C TCR transgenic T cells were transferred to these mice 10-14 days after tumor challenge. Tumor draining lymph nodes, non-draining lymph nodes, spleen and tumor tissue were collected 48, and 336 hours, as indicated, after 2C T cell transfer. T cells infiltrating tumors were isolated by a positive-selecting magnetic column. Cells from lymph nodes, spleen and tumor were subjected to FACS analysis after stained with antibody 1B2 and antibodies against activation markers CD62L or CD44. CD62L or CD44 expression by 1B2 positive 2C T cells was shown. D. OT-1/RAG-1$^{-/-}$ mice were injected with $10^6$ Ag104L$^d$ or Ag104L$^d$-LIGHT tumor cells subcutaneously. $3 \times 10^6$ 2C TCR transgenic T cells were transferred to these mice 10-14 days after tumor challenge. Adoptively transferred 2C T cells were able to suppress the growth of LIGHT$^m$-expressing Ag104L$^d$ in the OT-1/RAG-1$^{-/-}$ hosts but not the parental tumors.

To investigate what happens when adoptively transferred 2C T cells when LIGHT$^m$ is present inside the tumor environment. LIGHT$^m$-expressing Ag104L$^d$ tumors were rejected by endogenous CD8$^+$ T cells without 2C T cell transfer in C3B6F1 hosts. In order to trace antigen-specific T cells and monitor their trafficking, priming and ability to reject tumors, H—Y or OT-1 TCR transgenic mice in B6 (H-2$^b$)/RAG-1$^{-/-}$ background were used as recipients for tumor challenges. These mice harbor monoclonal CD8$^+$ T cells that do not respond to Ag104L$^d$ tumor. Thus, Ag104L$^d$ or LIGHT$^m$ expressing Ag104L$^d$ both grew aggressively in these mice similarly as in the RAG-1$^{-/-}$ mice (FIG. 7D). However, adoptively transferred 2C T cells do not undergo vigorous homeostatic proliferation up to 14 days under constant observation due to the presence of these CD8$^+$ H—Y or OT-1 transgenic T cells in these mice (FIG. 7B). Thus, the vigorous proliferation of 2C T cells in these hosts were antigen L$^d$ driven within 14 days after adoptive transfer. 10$^6$ Ag104L$^d$ or Ag104L$^d$-LIGHT$^m$, which expressed the same level of antigen L$^d$ on their surface (FIG. 7A), was subcutaneously inoculated into these mice. Then adoptively transferred 3×10$^6$ CFSE labeled 2C T cells to the mice 10-14 days after tumor challenge. Mice were sacrificed 48, 132, 168 and 336 hours after T cell transfer and tumor draining lymph nodes (DLN), other non-draining lymph nodes (NDLN), spleen (SPL) and tumor mass were collected. Single-cell suspension of tumor mass was obtained by collagenase digestion. If necessary, T cells infiltrating tumors (TIL) were purified with a positively selective magnetic system from tumor cells. 2C T cell trafficking and proliferation was evaluated. Naïve 2C T cells with high CFSE staining, high CD62L and low CD44 were present similarly in the secondary lymphoid organs in both Ag104L$^d$ or Ag104L$^d$-LIGHT$^m$ bearing mice 48 hours after T cell transfer (FIG. 7B & C). However, a significant number of naïve 2C T cells, which are CD62L$^{high}$ and CD44$^{low}$, were detected inside LIGHT$^m$-expressing tumors but not in the parental tumors (FIG. 7B & C). This population of 2C T cells proliferated inside LIGHT$^m$-expressing tumor indicated by the dilution of CFSE 132 hours after T cell transfer (FIG. 7B). At this time point, no 2C T cells, naïve or proliferated, could be detected in the parental tumors (FIG. 7B). At 168h after 2C T cell transfer, large amounts of proliferated 2C T cells were present solely in the LIGHT$^m$-expressing tumors. Up to 7 days (168h) after 2C T cell transfer, no significant CFSE-labeled 2C T cell proliferation or proliferated 2C T cells could be detected in the secondary lymphoid tissues of the mice bearing LIGHT$^m$-positive or negative tumors (FIG. 5B). Activation of 2C T cells by antigen L$^d$ did not happen in the tumor draining nodes, other lymph nodes or spleen, but only inside LIGHT$^m$-positive tumor. 14 days after 2C T cell transfer, CFSE-low, fully proliferated 2C T cells were detected in the secondary lymphoid organs of the mice bearing LIGHT$^m$-expressing tumors. The 2C T cells present in the lymph nodes expressed high level of CD44 and CD62L. However, the 2C T cells trafficking to the spleen were mixtures of CD44$^{high}$CD62$^{low}$ and CD44$^{high}$CD62L$^{high}$ populations (FIG. 5C). This result was consistent with previous findings that central memory T cells traffick to lymph node and both central and peripheral memory T cells can go to spleen (ref. Ahmed). In the mice bearing parental tumors, 2C T cells present in the secondary lymphoid organs maintained a naïve phenotype (CD$_{62}$L$^{high}$ and CD44$^{low}$) without significant proliferation after 14 days (FIG. 7B & C). Furthermore, no detectable 2C T cells, naïve or activated, present inside the parental tumors (FIG. 7B & C).

More importantly, 2C T cell proliferation correlated with tumor rejection. Ag104L$^d$-LIGHT$^m$ tumors established for 10 days in these H—Y transgenic mice were completely suppressed while the parental tumors grew comparably to those in mice without 2C T cell transfer (FIG. 7D).

C3B6F1 mice were used as tumor recipients. 5×10$^6$ Ag104L$^d$ or Ag104L$^d$-LIGHT was inoculated subcutaneously to C3B6F1 mice. 10-14 days later, 3×10$^6$ CFSE labeled 2C T cells were adoptively transferred into the hosts and trafficking and proliferation of the T cells in the tumor draining lymph nodes, other non-draining lymph nodes, spleen or tumor mass were checked after 48 hours and 168 hours. It yielded similar results as in H—Y or OT-1 TCR transgenic mice.

Naïve tumor antigen-specific T cells can be recruited to the tumor site and they proliferated there effectively and killed the tumor cells in the LIGHT$^m$-mediated environment even when the antigens are not well cross-presented. More significantly, these T cells were able to suppress tumor grow in situ. Interestingly, LIGHT$^m$-mediated tumor environment generated large amount of tumor antigen-specific T cells that were able to leave tumor site, re-circulate and potentially reject other tumors in the distal sites bearing the same antigen without LIGHT$^m$ (Table 3).

Figure 8:
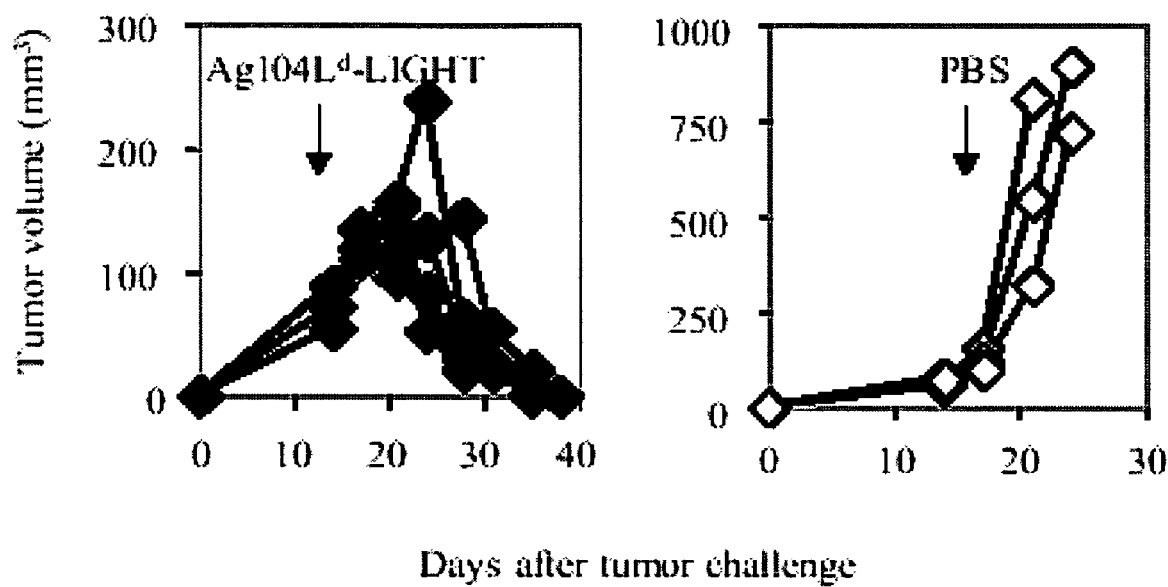
FIG. 8 shows that intra-tumor injection of LIGHT-expressing Ag104L$^d$ eradicates established parental tumors. $10^5$ Ag104L$^d$ tumor cells were inoculated to C3B6F1 mice followed by intra-tumor injection of $10^6$ LIGHT$^m$-expressing tumor cells or PBS as control as indicated 14 days after challenge of parental tumor. Ag104L$^d$ tumors treated with Ag104L$^d$-LIGHT$^m$ were rejected while the ones treated with PBS grew progressively.

Therapeutic vaccination with LIGHT$^m$-expressing Ag104L$^d$ eradicates established parental tumor LIGHT$^m$-mediated tumor environment was able to recruit naïve T cells and activate them inside the tumor and cause tumor rejection. The potential therapeutic efficacy of the finding was shown by injecting LIGHT$^m$-expressing tumor cells into the established parental tumor. Such treatment could create lymphoid environment to attract naïve T cells and then activate tumor specific ones via co-stimulation in the presence of antigen leading to the rejection of these established tumors. 10$^5$ Ag104L$^d$ was inoculated subcutaneously to C3B6F1 recipients and the tumors were allowed to establish for 14 days. Then 10$^6$ LIGHT$^m$-expressing Ag104L$^d$ tumor cells were injected inside the established parental tumors. As control, the same volume of PBS was injected into the tumors in the same way. The established parental tumors treated with LIGHT$^m$-expressing tumor cells continued to grow for 10-15 days before they started to regress and disappeared (FIG. 8). Ag104L$^d$ tumors treated with PBS grew aggressively.

LIGHT$^m$-mediated tumor environment generated many tumor antigen-specific central and effector memory T cells going back to circulation. The generation of such a pool of lymphocytes may be important to eradicate metastasis after surgical removal of primary tumors. Tumor antigen-specific memory T cells with high quantity from LIGHT$^m$-mediated environment may be able to reject established parental tumor in the distal site. To set up a clinically relevant model, 10$^4$ Ag104L$^d$ tumor cells was injected to the left flank of C3B6F1 hosts and the tumors were established for 20 days. 10$^6$ Ag104L$^d$-LIGHT$^m$ tumor cells were injected 20 days later to the right flank of the mice. Alternatively, the same volume of PBS was injected to the Ag104L$^d$-tumor bearing mice in the control group. 100% of the mice treated with LIGHT$^m$-bearing tumor cells rejected the established parental tumors. Ag104L$^d$ tumors grew progressively on the mice in the control group 100% (Table 2).

The therapeutic efficacy of LIGHT$^m$-expressing tumor cells was demonstrated in another model more closely simulated clinical metastasized tumors. 10$^6$ (primary tumor) and 5×10$^4$ (distal tumor) Ag104L$^d$ tumor cells were inoculated into the left and right flank of the recipient mice, respectively.

The primary tumor was surgically removed 14 days after tumor inoculation and $10^6$ LIGHT$^m$-expressing Ag104L$^d$ tumor cells were injected into the upper back of the mouse. Growth of the established distal tumor was observed. All the mice in the treated group rejected the distal tumors. However, without treatment with LIGHT$^m$-expressing tumor, the distal tumor killed all the hosts in the control group (Table 2).

LIGHT$^m$-mediated tumor environment is able to recruit naïve T cells and activated and expanded tumor antigen-specific T cells and reject tumor cells bearing the antigen in situ. Moreover, large amount of tumor antigen-specific central and effector memory-type T cells were generated inside the environment and able to traffick to distal sites to reject tumors bearing the same antigen (Table 3).

Delivery of mutant LIGHT (LIGHT$^m$) by adenovirus into tumor tissues allows effective immune response and tumor rejection.

Figure 10:
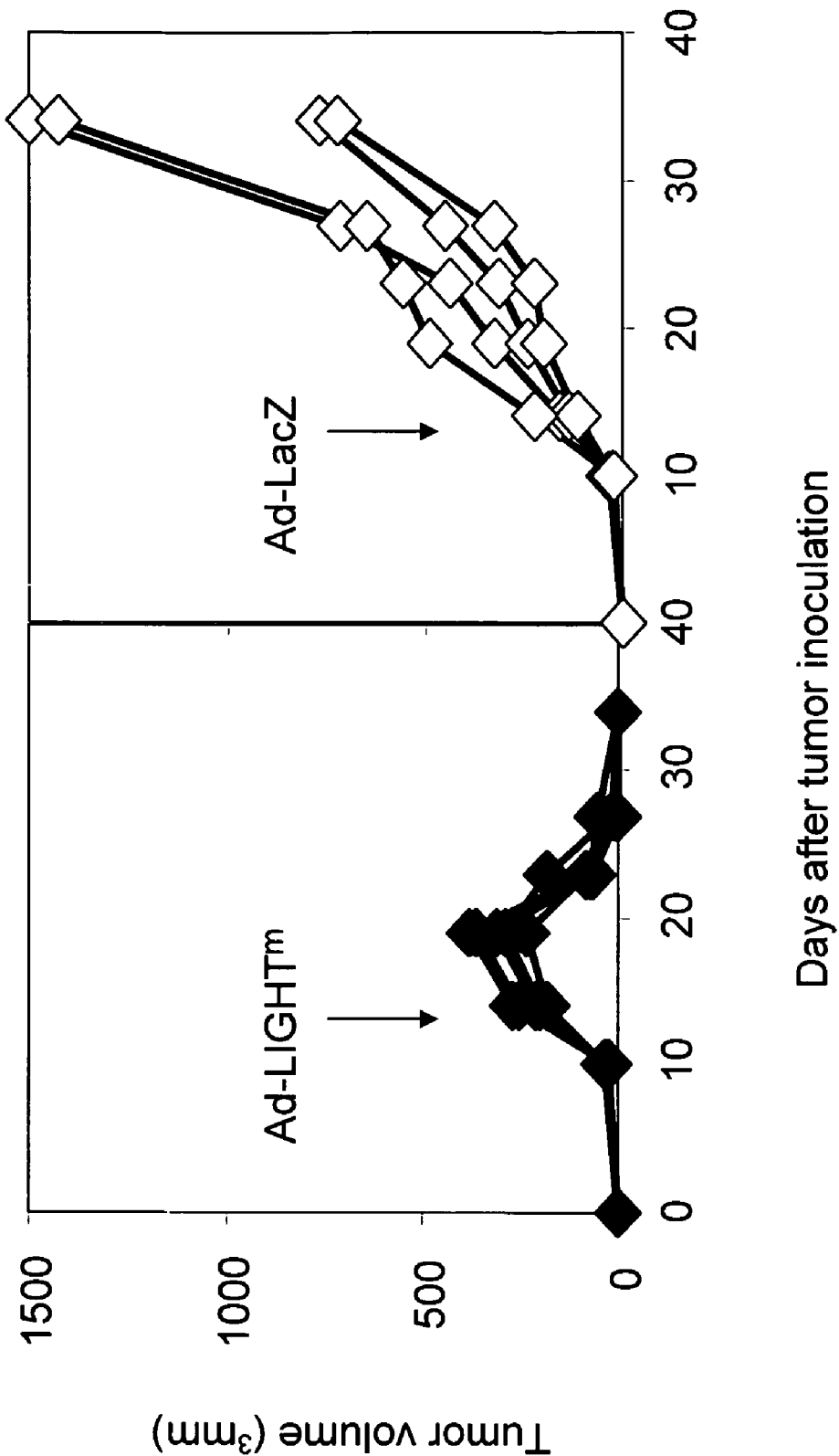
FIG. 10 shows that delivery of mutant LIGHT by adenovirus into tumor tissues allows effective immune response and tumor rejection. C3B6F1 mice were inoculated with $2 \times 10^5$ Ag104L$^d$ tumor cells, followed by an intratumoral injection of $5 \times 10^{10}$ LIGHT-expressing adenovirus (left) or LacZ-expressing adenovirus as indicated (right) 14 d after parental tumor challenge. Tumor volume was calculated by formula (length×width×height)/2.

FIG. 10 illustrates the reductions of tumor volume correlated with the presence in vivo of mutant LIGHT expression in tumor cells.

Figure 11:
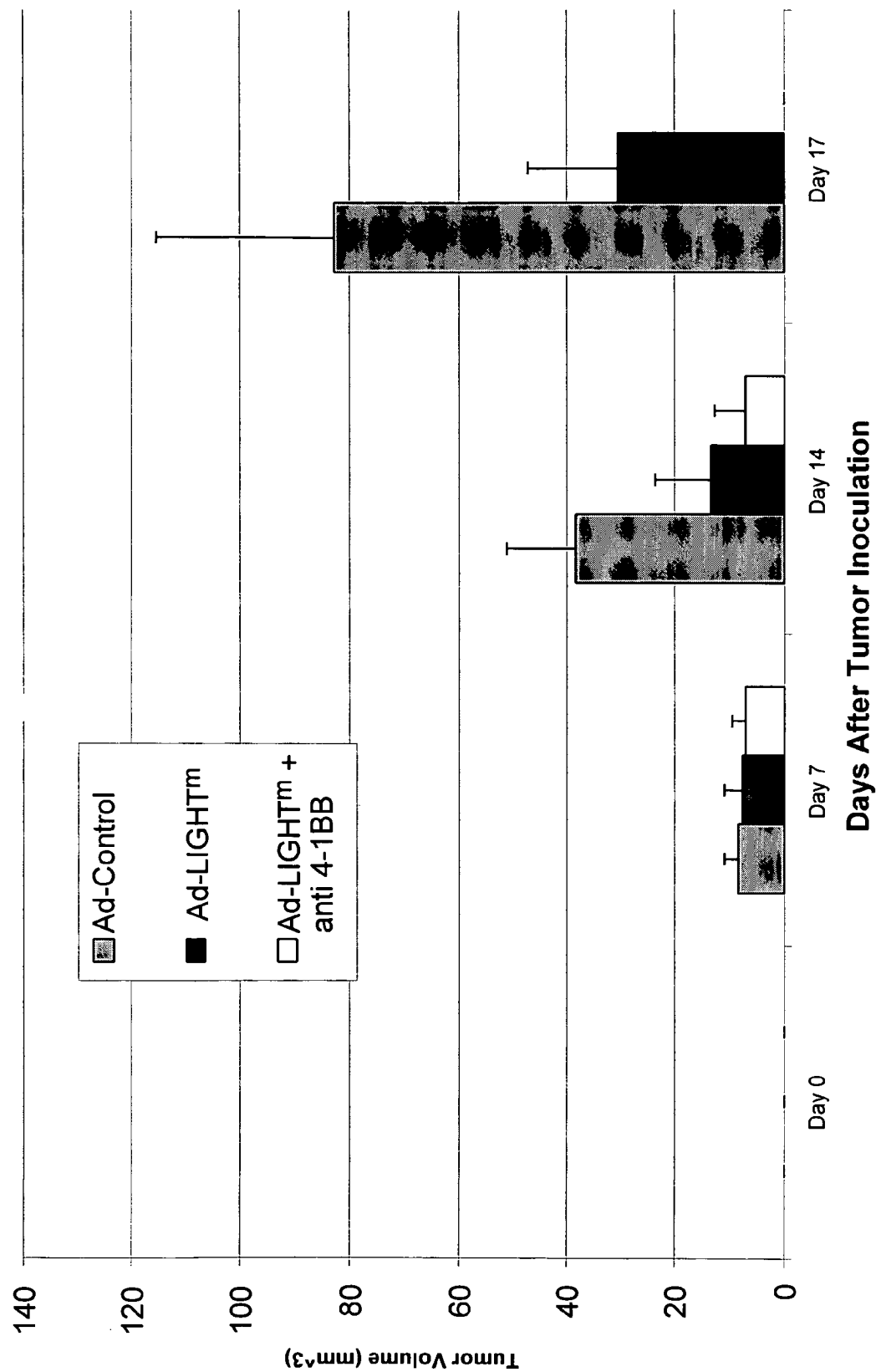
FIG. 11 shows inhibition of 4T1 tumor growth and reduction in spontaneous metastatic tumors. At Day 0 4T1 mice were inoculated with control, mutant LIGHT or LIGHT$^m$ and anti 4-1 BB. At Day 7 Ad-LIGHT$^m$ (or D10 2A) showed some reduction, at Days 14 and 17 this volume reduction was more pronounced. At Day 19 tumors are removed. At Day 34 tissues were checked for lung metastasis.

FIG. 11 illustrates reduction in spontaneous metastasis in mice at days 14, 17 and until day 34 after inoculation. There is a synergistic effect of anti-41BB, an antibody that stimulate T cells, on tumor reductions.

Figure 12:
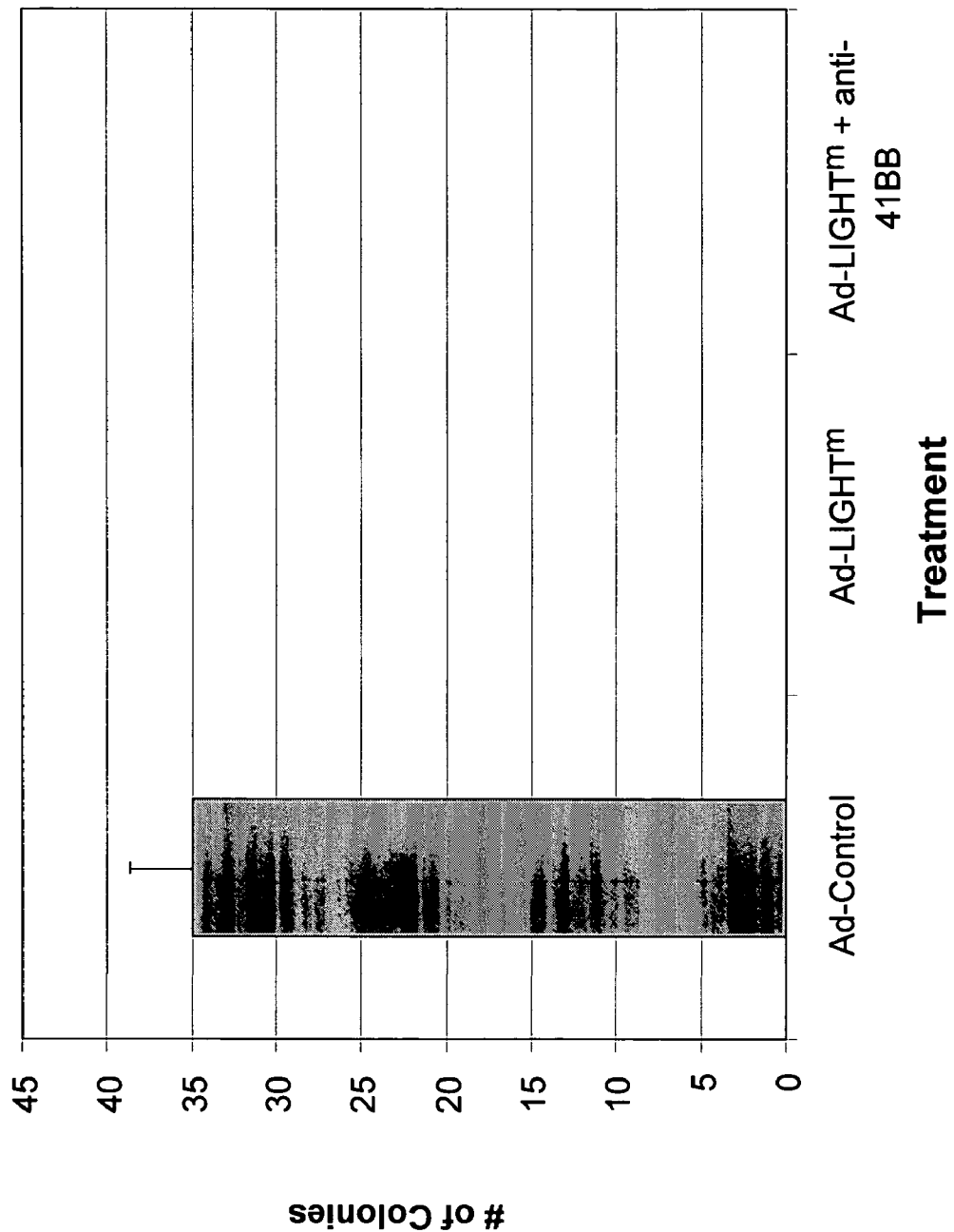
FIG. 12 shows results of a clonogenic assay of the treatment groups' of FIG. 11. Metastases in mice treated with Ad-mutant LIGHT$^m$ with and without 41 BB were prevented.

FIG. 12 shows that the clonogenic assay shows no evidence of metastasis after mutant LIGHT treatment.

TABLE 1

LIGHT augments host's resistance to Ag104L$^d$ tumor challenges

| Tumor cells injected[a] | | Incidence of tumor growth[b] | (Percentage) |
|---|---|---|---|
| Ag104L$^d$ | $5 \times 10^6$ | 10/10 | (100) |
| | $1 \times 10^6$ | 11/11 | (100) |
| | $5 \times 10^5$ | 10/10 | (100) |
| | $1 \times 10^5$ | 5/5 | (100) |
| | $5 \times 10^4$ | 4/4 | (100) |
| | $1 \times 10^4$ | 4/4 | (100) |
| Ag104L$^d$-LIGHT | $5 \times 10^5$ clone H10 | 0/10 | (0) |
| | $1 \times 10^6$ clone H10 | 0/11 | (0) |
| | $5 \times 10^6$ clone H10 | 0/10 | (0) |
| | $5 \times 10^6$ bulk | 0/10 | (0) |

[a]Number of tumor cells as indicated were injected subcutaneously to C3B6F1 mice.
[b]The results were pooled from 1 to 3 independent experiments.

TABLE 2

Incidence of Ag104L$^d$ tumors in C3B6F1 mice

| Tumor cells injected/Treatment | Incidence of tumor growth[a] | (Percentage) |
|---|---|---|
| $10^6$ Ag104L$^d$/no treatment | 16/16 | (100) |
| $10^6$ Ag104L$^d$/CD8-depletion[b] | 6/6 | (100) |
| $10^6$ Ag104L$^d$-LIGHT/no treatment | 0/6 | (0) |
| $10^6$ Ag104L$^d$-LIGHT/CD8-depletion[b] | 6/6 | (100) |
| $10^6$ Ag104L$^d$-LIGHT/LTβR-Ig[c] | 6/6 | (100) |
| $10^7$ Ag104L$^d$/$10^6$ Ag104L$^d$-LIGHT 40 days ago | 0/5 | (0) |
| $10^7$ Ag104L$^d$/$10^6$ Ag104L$^d$-LIGHT 60 days ago | 0/5 | (0) |

[a]The results were pooled from 1 to 4 independent experiments.
[b]CD8+ cells were depleted by anti-CD8 antibody. Depletion was confirmed by checking peripheral blood samples.
[c]100 μg of LTβR-Ig was injected on the day of tumor challenge to each recipient.

TABLE 3

Treatment with Ag104L$^d$-LIGHT eradicates established tumors at the distal sites

| Ag104L$^d$ tumor cells injected | Days of tumor establishment[a] | Treatment | Incidence of tumor growth | (Percentage) |
|---|---|---|---|---|
| $10^4$ | 20 days | No treatment | 4/4 | (100) |
| $10^4$ | 20 days | $10^6$ Ag104L$^d$-LIGHT[b] | 0/4 | (0) |
| $5 \times 10^4$ | 20 days | No treatment | 4/4 | (100) |
| $5 \times 10^4$ | 20 days | $10^6$ Ag104L$^d$-LIGHT[b] | 2/4 | (50) |
| $10^6$ (primary) + $5 \times 10^4$ (distal) | 14 days | Surgical removal of primary tumor | 4/4 | (100) |
| $10^6$ (primary) + $5 \times 10^4$ (distal) | 14 days | Surgical removal of primaly tumor & $10^6$ Ag104L$^d$-LIGHT[b] | 0/4 | (0) |
| $5 \times 10^6$ (primary) + $10^6$ (distal) | 20 days | Surgical removal of primary tumor | 4/4 | (100) |
| $5 \times 10^6$ (primary) + $10^6$ (distal) | 20 days | Surgical removal of primary tumor & $10^6$ Ag104L$^d$-LIGHT[b] | 2/4 | (50) |

[a]Days of growth of subcutaneously injected Ag104L$^d$ in the hosts before treatment started
[b]$10^6$ Ag104L$^d$-LIGHT tumor cells were injected subcutaneously at other site than where Ag104L$^d$ grew.

Materials and Methods

Mice, Cell Lines, and Reagents. Female C3HXC57BL/6 F1 (C3B6F1) mice, 4-8 weeks old were purchased from the National Cancer Institute, Frederick Cancer Research Facility, (Frederick, Md.). C57BL/6-RAG-1-deficient (RAG-1$^{-/-}$) mice were purchased from the Jackson Laboratory (Bar Harbor, Me.). H—Y TCR transgenic mice (H—Y mice) on the RAG-2-deficient/B6 background were purchased from Taconic Farms (Germantown, N.Y.). 2C TCR transgenic mice on RAG-1-deficient background bred into B6 for 10 generations (2C mice) were provided by J. Chen (Massachusetts Institute of Technology, Boston, Mass.). OT-1 TCR transgenic mice (OT-1 mice) were provided by A. Ma (The University of Chicago). RAG-1$^{-/-}$, H—Y,2C, OT-1 mice were bred and maintained in the specific pathogen-free facility at the University of Chicago. Animal care and use were in accord with institutional guidelines.

The AG104A fibrosarcoma grew out spontaneously in an aging C3H mouse and was adapted to culture as described (Ward 1989 JEM). The AG104A expressing murine H-2L$^d$ (AG104-L$^d$), the transfectant of AG104A cells, has been described previously (Wick M, 1997, JEM). These tumor cell lines were maintained in DMEM (Mediatech) supplemented with 10% FCS (Sigma-Aldrich), 100 U/ml penicillin, and 100 μg/ml streptomycin (BioWhittaker). The hybridoma cell lines producing anti-L$^d$ (clone 30-5-7) and anti-2C TCR (1B2)

antibodies were obtained from D. Sachs (National Institutes of Health, Bethesda, Md.) and T. Gajweski (The University of Chicago), respectively.

Monoclonal antibodies produced by hybridomas were purified from the culture supernatant with protein G column by standard procedure. The 1B2 antibody was conjugated to FITC or biotin by the Monoclonal Antibody Facility of The University of Chicago. PE-coupled anti-CD8 antibody, Cychrome (CyC)-coupled streptavidin, CyC-coupled anti-CD44 antibody, PE-coupled anti-CD62L antibody and PE-coupled Th1.2 antibody were purchased from BD Biosciences. FITC-conjugated-goat-anti-mouse IgG was purchased from Caltag. PE-coupled streptavidin was purchased from Immunotech. PE-coupled donkey anti-human IgG was purchased from Jackson Immunological Research Lab (West grove, Pa.). Biotinylated goat anti-SLC antibody was purchased from R&D systems Inc. (Minneapolis, Minn.). AP conjugated rabbit anti-goat Ig antibody was purchased from Vector Laboratories Inc. (Burlingame, Calif.). Purified goat anti-SLC antibody was purchased from Pepro-Tech (Rock hill, N.J.). Collagenase (type 4) was purchased from Sigma-Aldrich. CFSE was purchased from Molecular Probes.

HVEM-Ig and LTβR-Ig fusion proteins used in this study have been described previously (jing's JCI and Q. Wu JEM 1999).

Generation of B7.1 or mutant LIGHT$^m$ Expression Vectors and Clones To generate pMFG-S-mutant LIGHT$^m$, pcDNA3.1-mutant LIGHT$^m$ was digested with NcoI and BamHI and ligated to a NcoI and BamHI-digested the pMFG-S-TPA plasmid (Dr. Mulligan R. C., Massachusetts Institute of Technology, Boston, Mass.). φNxEco packaging cells producing the viruses containing mutant LIGHT$^m$ was generated by transient transfection with MFG-S-mutant LIGHT$^m$ by calcium precipitation method. The expression of mutant LIGHT$^m$ by infected AG104L$^d$ tumor cells (AG104L$^d$-LIGHT$^m$ bulk) was assayed by staining the cells with a rabbit anti-serum recognizing mutant LIGHT$^m$. Subsequently, the infected mutant LIGHT$^m$-expressing AG104L$^d$ tumor cells were cloned by limiting dilution method. AG104L$^d$-LIGHT$^m$ clone H10 was one of these clones used in the experiments.

Tumor Growth In Vivo Tumor cells were injected subcutaneously into the lower back, that is, 0.5-1 cm above the tail base of the mice. Tumor growth was measured every 3 to 4 days with a caliper. Size in cubic centimeters was calculated by the formula $V=\pi abc/6$, where a,b, and c are three orthogonal diameters.

Histology Tumor tissues for histology examination were collected at time indicated and fixed in 10% neutral buffered formalin, processed to paraffin embedment, and stained with hematoxylin and eosin. For immunohistochemical staining of SLC, tumor tissues were harvested, embedded in OCT compound (Miles-Yeda, Rehovot, Israel) and frozen at −70° C. Frozen sections (5-10 μm thick) were fixed in cold 2% formalin in PBS and permeablized with 0.1% saponin/PBS. The sections were preblocked with 5% goat serum in 0.1% saponin/PBS for half an hour at room temperature in a humidified chamber. Staining for SLC was done by first incubating with biotinylated goat anti-SLC antibody (R&D systems Inc. Minneapolis, Minn.) at a ½5 dilution in blocking buffer. Alkaline phosphatase conjugated rabbit anti-goat Ig antibody (Vector Laboratories Inc. Burlingame, Calif.) was added 2 h later. For immunofluorescence staining, sections were blocked with 2% normal mouse serum, rabbit serum, and goat serum in PBS for half an hour at room temperature in a humidified chamber. Blocking solution was replaced with 50 μl of primary Abs, PE-conjugated anti-Th1.2 (BD PharMingen), or PE-conjugated anti-CD8 (BD PharMingen), diluted 1/100 in blocking solution, and sections were incubated for 1 h at room temperature in a humid chamber. Specimens were mounted in Mowiol 4-88 (BD Biosciences, La Jolla, Calif.) containing 10% 1,4-diazobicyclo [2.2.2] octane. Samples were analyzed within 48 h using a Zeiss Axioplan microscope (Zeiss, Oberkochen, Germany) and a Photometrics PXL$^d$ CCD camera (Photometrics, Tucson, Ariz.). No-neighbor deconvolution was performed using Openlab v2.0.6 (Improvision, Lexington, Mass.).

ELISA for CCL21. Tumor homogenates were prepared and assayed for CCL21. Comparable amount of tumor tissues from tumor-bearing mice were collected and weighed, homogenized in PBS that contained protease inhibitors, and the supernatants were collected by centrifugation. Polystyrene 96-well microtiter plates (Immulon 4, Dynatech Laboratories, Chantilly, Va.) were coated with goat anti-mouse CCL21 at 2μ μg/ml in PBS and were then blocked with 0.1% bovine serum albumin (BSA) in PBS for 30 min at room temperature. After washing, serial dilutions of standards of known concentrations (Recombinant CCL21, 50 ng/ml, R&D) and samples were added and incubated for 2 h at room temperature. After 3 washes, biotinylated rabbit anti-SLC Ab was added to the wells. After 2h incubation and washing, 50 μl of a ⅟1000 diluted alkaline phosphatase-conjugated avidin (Dako) was added for 1 h and then developed. Color development was measured at 405 nm on an automated plate reader (Spectra-Max 340, Molecular Devices, Sunnyvale, Calif.) and The amount of CCL21 was determined by ELISA from the standard curve, and normalized according to tissue weight. Data are mean±s.d.

Real-time quantitative RT-PCR assay. Real-time PCR was performed. Total RNA from tumors was isolated with Absolute RNA miniprep Kit (Stratagene, La Jolla, Calif.) and digested with DNaseI (Life Technologies, Grand Island, N.Y.) to remove chromosomal DNA. The remaining DNaseI was inactivated at 75° C. for 20 min and integrity of RNA was assessed by visualization of ethidium bromide-stained gels. 5 μg of total RNA was reverse transcribed into cDNA with the First Strand cDNA Synthesis kit (Amersham Pharmacia, Piscataway, N.J.). The real-time quantitative PCR analysis was done on the ABI Prism 7700-sequence detection system (PE Applied Biosystems). The primer sequences for CCL21 were 5'-AGACTCAGGAGCCCAAAGCA-3' (forward primer) (SEQ ID NO: 2) and 5'-GTTGAAGCAGGGCA AGGGT-3' (reverse primer) (SEQ ID NO: 3), and the probe for CCL21 was 5'-CCACCTCATGCTGGCCTCCGTC-3' ISEQ ID NO: 4). The primers for MAdCAM-1 were 5'-GACACCAGCT-TGGGCAGTGT-3' (forward primer) (SEQ ID NO: 5) and 5'-CAGCATGCCCCGTACAGAG-3' (reverse primer) (SEQ ID NO: 6), and the probe for MAdCAM-1 was 5'-CAGAC-CCTCCCAGGCAGCAGTATCC-3' (SEQ ID NO: 7). The primers for GAPDH were 5'-TTCACCACCATG-GAGAAGGC-3' (forward primer) (SEQ ID NO: 8) and 5'-GGCATGGACT GTGGTCATGA-3' (reverse primer) (SEQ ID NO: 9), and the probe for GAPDH was 5'-TGCATC-CTG CACCACCAACTGCTTAG-3' (SEQ ID NO: 10). The CCL21 and MAdCAM-1 probes were labeled with 6-carboxy-fluorescein (FAM). The GAPDH probe was labeled with tetrachloro-6-carboxy-fluorescein (TET). Each cDNA sample was amplified in duplex for CCL21 and GAPDH or MAdCAM-1 and GAPDH with the TaqMan Universal PCR master mixture containing AmpliTaq Gold DNA Polymerase according to the manufacturer's instructions (PE Applied Biosystems). PCR conditions were 2 min at 50° C., 10 min at 95° C., 15 s at 95° C. and 1 min at 60° C. for 40 cycles. The concentration of target gene was determined using the comparative $C_T$ (threshold cycle number at cross-point between amplification plot and threshold) method and normalized to the internal GAPDH control.

Tumor tissue chemokine microarray For these experiments, GEArray Q series Mouse Chemokines and Receptors Gene Array membrane (SuperArray, Bethesda, Md.) were used. Total RNA from tumors was isolated with Absolute RNA miniprep Kit (Stratagene, La Jolla, Calif.) and digested with DNaseI (Life Technologies, Grand Island, N.Y.) to remove chromosomal DNA. The remaining DNaseI was inactivated at 75° C. for 20 min. Integrity of RNA was assessed by visualization of ethidium bromide-stained gels. The microarrays were employed according to the manufacturer's instructions. In brief, using reagents provided, cDNA was prepared from total RNA by reverse transcription with MMLV reverse transcriptase, radiolabeled using [−32P] dCTP (3,000 Ci/mM), then hybridized under precisely specified conditions to a positively charged nylon membrane containing the arrayed DNA. After washing, the arrays were visualized by phosphorimager. Loading was adjusted based on intensity of hybridization signals to the housekeeping genes, PUC18,actin and GAPDH, then gene expression was quantitated after the digital image recorded by phosphorimager was converted to digital data by using ImageQuant software. The raw data was analyzed using the GEArrayAnalyzer software according to manufacturer's instructions.

T-cell co-stimulation assay. T cells were purified by a negative selection method in the magnetic field as instructed by the manufacture (Miltenyi Biotec, Auburn, Calif.). The purity of isolated T cells was greater than 95%, as assessed by flow cytometry using monoclonal antibody against CD3. Plates coated with 0.2 g/ml monoclonal antibody against CD3 were further coated at 37° C. for 4 h with LIGHT$^m$-flag. After being washed, purified T cells (1×106 cells/ml) were cultured in the wells. Monoclonal antibody against CD28 (1 µg/ml) was used in soluble form. In all assays, the proliferation of T cells was assessed by the addition of 1 Ci/well$^3$H-thymidine during the last 15 h of the 3-day culture. $^3$H-thymidine incorporation was measured in a TopCount microplate scintillation counter (Packard instrument, Meriden, Conn.).

Analysis of Cells by FACS. In order to confirm that mutant LIGHT$^m$ binds to LTbR and HVEM, AG104L$^d$ tumor cells transfected with mutant LIGHT (AG104L$^d$-LIGHT$^m$) were incubated with LTbR-Ig or HVEM-Ig (0.02mg/mL), washed, and stained with PE-coupled donkey anti-human IgG or FITC-coupled goat anti-mouse IgG, respectively. For analysis of L$^d$ expression, tumor cells were incubated with the anti-L$^d$ antibody, washed, and incubated with FITC-coupled anti-mouse IgG antibody. For detection of proliferation of CFSE-labeled 2C T cells, isolated lymph node (LN) cells, splenocytes, and tumor-infiltrating T cells (TIL) were stained with biotinylated 1B2 antibody, washed, and stained with CyC-coupled streptavidin and PE-coupled anti-CD8. For analysis of CFSE-labeled 2C T cells and CD44 expression, isolated LN cells, splenocytes or TIL$^d$ were stained with biotinylated 1B2 antibody, washed, and stained with a mixture of PE-coupled streptavidin and CyC-coupled anti-CD44. For analysis of CFSE-labeled 2C T cells and CD62L expression, isolated LN cells, splenocytes or TIL$^d$ were stained with biotinylated 1B2 antibody, washed, and stained with CyC-coupled streptavidin and PE-coupled anti-CD62L. Samples were analyzed on a FACScan and data was analyzed with CELLQuest or FlowJo softwares.

Adoptive Transfer of 2C T Cells. LN cells and splenocytes were isolated from 2C mice and CD8$^+$ T cells were negatively selected with a CD8$^+$ T cell enrichment kit (Miltenyi Biotec, Auburn, Calif.). When analyzed, >90% of the enriched CD8$^+$ cells expressed the 2C receptor. Approximately 3×10$^6$ 2C T cells were transferred into H—Y or OT-1 mice for assays of tumor growth. The same number of 2C T cells was transferred to each mouse in each experiment. To transfer CFSE-labeled T cells, T cells at a concentration of 2×10$^7$/ml were labeled with 10 µM CFSE in PBS at 37° C. for 30 min. The cells were quenched with equal volume of FCS for 1 min and washed three times, and 3×10$^6$ CFSE-labeled T cells were injected intravenously into the retro-orbital plexus in a 0.2-ml volume to the tumor-bearing mice. Cells were isolated from the inguinal lymph nodes (DLNs), the other lymph nodes (non-draining lymph nodes [NDLN]), spleen or tumors at the time indicated.

Cell depletions and in vivo blockage of LIGHT$^m$ activity with LTbR-Ig Mice were depleted of lymphocyte subsets by standard procedures (current protocol for immunology) using monoclonal antibody (mAb) GK1.5 (Dialynas DM JI 1983) for CD4+ cells, and mAb 2,34 for CD8$^+$ cells (Sarmiento M 1980 JI). Examination of splenocytes and lymph node cells by FACS revealed that the depleted subset represented <0.5 % of the total lymphocytes, with normal levels of other subsets. To block LIGHT$^m$ in mice, the LT1$^3$R-Ig (100 µg/injection) were given the same day and a week after tumor challenge, intra-peritoneally.

Cell Isolation from tumor tissue. The mice were first bled to decrease the blood contamination of tumor tissue. The tumor tissues were collected, washed in the PBS, cut into pieces, and resuspended in DMEM supplemented with 2% FCS and 1.25 mg/ml collagenase D (collagenase D solution) for 40 min in a 37° C. shaking incubator. The single cell suspension was collected after 40 min, and the cell clumps were digested for another 40 min in the collagenase D solution until all tumor tissue had resolved into a single cell suspension.

Delivery of LIGHT$^m$ and LIGHT$^m$ expressing cells.

Delivery of a nucleic acid encoding LIGHT$^m$ into a patient may be either direct, in which case the patient is directly exposed to the nucleic acid or nucleic acid-carrying vectors, or indirect, in which case, tumor cells obtained from a biopsy are first transformed with the nucleic acids in vitro, irradiated and then transplanted into the patient. These approaches are routinely practiced in gene therapies for suppressing tumors or treating other illness.

Delivery of nucleic acids. The nucleic acid sequences are directly administered in vivo, where they are expressed to produce the encoded products. This can be accomplished by any of numerous methods known in the art, e.g., by constructing them as part of an appropriate nucleic acid expression vector and administering it so that they become intracellular, e.g., by infection using defective or attenuated retroviral or other viral vectors (U.S. Pat. No. 4,980,286), or by direct injection of naked DNA, or by use of microparticle bombardment, or coating with lipids or cell-surface receptors or transfecting agents, encapsulation in liposomes, microparticles, or microcapsules, or by administering them in linkage to a peptide which is known to enter the nucleus, by administering it in linkage to a ligand subject to receptor-mediated endocytosis (which can be used to target cell types specifically expressing the receptors), etc. Alternatively, the nucleic acid can be introduced intracellularly and incorporated within host cell DNA for expression, by homologous recombination.

Biodegradable microspheres have also been used in gene delivery that encapsulate the nucleic acid. Microspheres such as matrices, films, gels and hydrogels which include hyaluronic acid (HA) derivatized with a dihydrazide and crosslinked to a nucleic acid forming slow release microspheres have been used to deliver nucleic acids. U.S. Pat. No. 6,048,551 discloses a controlled release gene delivery system utilizing poly (lactide-co-glycolide) (PLGA), hydroxypropylmethyl cellulose phthalate, cellulose acetate phthalate, and copolymer microspheres to encapsulate the gene vector.

The therapeutic compositions used in the practice of the foregoing methods can be formulated into pharmaceutical compositions comprising a carrier suitable for the desired delivery method. Suitable carriers include materials that when combined with the therapeutic composition retain the anti-tumor function of the therapeutic composition. Examples include, but are not limited to, any of a number of standard pharmaceutical carriers such as sterile phosphate buffered saline solutions, bacteriostatic water, and the like. Therapeutic formulations can be solubilized and administered via any route capable of delivering the therapeutic composition to the tumor site. Potentially effective routes of administration include, but are not limited to, intravenous, parenteral, intraperitoneal, intramuscular, intratumor, intradermal, intraorgan, orthotopic, and the like. A preferred formulation for intravenous injection comprises the therapeutic composition in a solution of preserved bacteriostatic water, sterile unpreserved water, and/or diluted in polyvinylchloride or polyethylene bags containing sterile sodium chloride for injection. Therapeutic protein preparations can be lyophilized and stored as sterile powders, preferably under vacuum, and then reconstituted in bacteriostatic water (containing for example, benzyl alcohol preservative) or in sterile water prior to injection. Dosages and administration protocols for the treatment of cancers using the foregoing methods will vary with the method and the target cancer, and will generally depend on a number of other factors appreciated in the art.

Delivery using viral vectors. Viral vectors that contains nucleic acid sequences encoding an antibody of the invention are used for delivering specific nucleic acids. For example, a retroviral vector can be used. These retroviral vectors contain the components necessary for the correct packaging of the viral genome and integration into the host cell DNA. The nucleic acid sequences encoding the desired protein to be used in gene therapy are cloned into one or more vectors, which facilitates delivery of the gene into a patient. Adenoviruses are other viral vectors that can be used in gene therapy. Adenoviruses are especially attractive vehicles for delivering genes to respiratory epithelia and other targets for adenovirus-based delivery systems are liver, the central nervous system, endothelial cells, and muscle. Adenoviruses have the advantage of being capable of infecting non-dividing cells. Adeno-associated virus (AAV) has also been proposed for use in gene therapy (U.S. Pat. No. 5,436,146). Lentaviruses are promising for use in gene therapy.

Transfecting cells in tissue culture followed by delivery to patients. Another approach to gene therapy involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a patient. In this method, the nucleic acid is introduced into a cell prior to administration in vivo of the resulting recombinant cell. Such introduction can be carried out by any method known in the art, including but not limited to transfection, electroporation, microinjection, infection with a viral or bacteriophage vector containing the nucleic acid sequences, cell fusion, chromosome-mediated gene transfer, microcell-mediated gene transfer, spheroplast fusion, etc. The technique should provide for the stable transfer of the nucleic acid to the cell, so that the nucleic acid is expressible by the cell and preferably heritable and expressible by its cell progeny.

The resulting recombinant cells may be irradiated and can be delivered to a patient by various methods known in the art. Recombinant cells (e.g., hematopoietic stem or progenitor cells) are preferably administered intravenously. The amount of cells envisioned for use depends on the desired effect, patient state, etc., and can be determined by one skilled in the art. Cells into which a nucleic acid can be introduced for purposes of gene therapy encompass any desired, available cell type, and include but are not limited to epithelial cells, endothelial cells, keratinocytes, fibroblasts, muscle cells, hepatocytes, blood cells such as T lymphocytes, B lymphocytes, monocytes, macrophages, neutrophils, eosinophils, megakaryocytes, granulocytes; various stem or progenitor cells, in particular hematopoietic stem or progenitor cells, e.g., as obtained from bone marrow, umbilical cord blood, peripheral blood, fetal liver, etc.

Vaccines. As used herein, the term "vaccine" refers to a composition (e.g., a LIGHT$^m$ antigen and an adjuvant) that elicits a tumor-specific immune response. These vaccines include prophylactic (preventing new tumors) and therapeutic (eradicating parental tumors). A vaccine vector such as a DNA vaccine encoding mutant LIGHT can be used to elicit immune response against tumors. The response is elicited from the subject's own immune system by administering the vaccine composition at a site (e.g., a site distant from the tumor). The immune response may result in the eradication of tumor cells in the body (e.g., both primary and metastatic tumor cells). Methods for generating tumor vaccines are well known in the art (See e.g., U.S. Pat. Nos. 5,994,523 and 6,207,147 each of which is herein incorporated by reference).

The vaccines may comprise one or more tumor antigens in a pharmaceutical composition. In some cases, the tumor antigen is inactivated prior to administration. In other embodiments, the vaccine further comprises one or more additional therapeutic agents (e.g., cytokines or cytokine expressing cells).

In certain cases, cells selected from a patient, such as fibroblasts, obtained, for example, from a routine skin biopsy, are genetically modified to express one or of the desired protein. Alternatively, patient cells that may normally serve as antigen presenting cells in the immune system such as macrophages, monocytes, and lymphocytes may also be genetically modified to express one or more of the desired antigens. The antigen expressing cells are then mixed with the patient's tumor cells (e.g., a tumor antigen), for example in the form of irradiated tumor cells, or alternatively in the form of purified natural or recombinant tumor antigen, and employed in immunizations, for example subcutaneously, to induce systemic anti-tumor immunity. The vaccines may be administered using any suitable method, including but not limited to, those described above.

Clonogenic assay.

Clonogenic Assay for the Lung

Materials:
1) DMEM 5% FCS (+p/s, HEPES)
2) Collagenase type IV (Sigma)
3) 60 μM 6-thioguanine
4) 50 ml conical tubes
5) 6 well tissue culture plates
6) 37° C. shaking incubator/tissue culture incubator
7) dissecting equipment: scissors, curved scissors, and forceps
8) 70 μm nylon cell strainers 9) ACK lysis
10) methanol
11) 0.03% (w/v) methylene blue solution Note: all solutions and equipment must be sterile and aseptic technique should be used accordingly.

Prepare Collagenase Medium:
To approx 25 ml medium per number of lung, add collagenase to make the medium 1.5 mg/ml concentration.

Prepare Lung Sample:
1. Remove lung from mouse and transfer it to a 6 well plate
2. Add approx 200 ul of medium on the lung
3. With curved scissors, mince the lung into small pieces
4. Use the curved portion of the closed scissors, transfer minced lung into a 50 ml conical tube 5 ml of collagenase medium.
5. Add 5 ml of medium to the wells and pipette out and transfer the remaining lung pieces to the conical tube
6. Place in shaking incubator for 20 minutes at 37° C. at 175 rpm
7. Pour the supernatant through a cell strainer into a clean 50 ml conical tube-any lung pieces on the cell strainer should return to the conical tube for a second digestion
   a. Tube with sup from the digestion, spin down at 1500 rpm for 5 min in centrifuge.
   b. Discard sup after spinning down.
   c. Resuspend pellet in 1 ml of fresh collagenase free medium
8. ACK lysis for 5 minutes
9. Count cells
10. Plate 3×10^5, 3×10^4, 3×10^3 cells into 12 well plate
11. Add 60 μM 6-thioguanine into each well
12. Place plate in 37° C. tissue culture incubator, 5% $CO_2$ for 5-10 days Harvest Clonogenic Metastatic Colonies:

(Not Necessary But Easier to Count Colonies)
1. Discard culture media from tissue culture plate
2. Fix cells by adding 5 ml of methanol to each plate and swirl. Incubate at room temperature for 5 min
   a. NOTE: Colonies should turn white
3. Discard methanol and rinch each plate gently with 5 ml distilled water
   a. Important NOTE: Do not let the cells come in contact with water until after the cells have been fixed
4. Add 5 ml 0.03% (w/v) methylene blue solution to each plate. Swirl to cover entire plate and incubate at room temperature for 5 min
5. Discard dye and rinse plate gently with 5 ml distilled water
6. Allow plate to air dry before counting blue colonies
One colony represents one clonogenic metastatic cells Publications Cited The publications cited are incorporated by reference to the extent they relate to the present invention.

Boon, T. & van der Bruggen, P. Human tumor antigens recognized by T lymphocytes. *J. Exp. Med.* 183, 725-29 (1996).

Cannon, R. E. et al. Induction of transgene expression in Tg.AC(v-Ha-ras) transgenic mice concomitant with DNA hypomethylation. *Mol Carcinog* 21, 244-50 (1998).

Chen, L., Linsley, P. S. & Hellstrom, K. E. Costimulation of T cells for tumor immunity. *Immunol Today* 14, 483-6. (1993).

Cyster, J. G. Chemokines and cell migration in secondary lymphoid organs. *Science* 286, 2098-102. (1999).

Dougall, W. C. et al. RANK is essential for osteoclast and lymph node development. *Genes Dev* 13, 2412-24. (1999).

Ettinger, R. The role of tumor necrosis factor and lymphotoxin in lymphoid organ development. *Curr Top Microbiol Immunol* 251, 203-10 (2000).

Fu, Y. X. & Chaplin, D. D. Development and maturation of secondary lymphoid tissues. *Annu Rev Immunol* 17, 399-433 (1999).

Kang, H. S. et al. Signaling via LTbetaR on the lamina propria stromal cells of the gut is required for IgA production. *Nat Immunol* 3, 576-82 (2002).

Kim, D. et al. Regulation of peripheral lymph node genesis by the tumor necrosis factor family member TRANCE. *J Exp Med* 192, 1467-78. (2000).

Kong, Y. Y. et al. Activated T cells regulate bone loss and joint destruction in adjuvant arthritis through osteoprotegerin ligand. *Nature* 402, 304-9. (1999).

Leder, A., Kuo, A., Cardiff, R. D., Sinn, E. & Leder, P. v-Ha-ras transgene abrogates the initiation step in mouse skin tumorigenesis: effects of phorbol esters and retinoic acid. *Proc. Natl. Acad. Sci. U. S. A.* 87, 9178-82 (1990).

Mauri, D. N. et al. LIGHT, a new member of the TNF superfamily, and lymphotoxin alpha are ligands for herpesvirus entry mediator. *Immunity* 8, 21-30. (1998).

Melero, I. et al. Monoclonal antibodies against the 4-1BB T-cell activation molecule eradicate established tumors. *Nat Med* 3, 682-5. (1997).

Ochsenbein, A. F. et al. Roles of tumour localization, second signals and cross priming in cytotoxic T-cell induction. *Nature* 411, 1058-64. (2001).

Ostrand-Rosenberg, S. et al. Cell-based vaccines for the stimulation of immunity to metastatic cancers. *Immunol Rev* 170, 101-14. (1999).

Peace, D. J. et al. Lysis of ras oncogene-transformed cells by specific cytotoxic T lymphocytes elicited by primary in vitro immunization with mutated ras peptide. *J Exp Med* 179, 473-9 (1994).

Rooney, I. A. et al. The lymphotoxin-beta receptor is necessary and sufficient for LIGHT-mediated apoptosis of tumor cells. *J Biol Chem* 275, 14307-15. (2000).

Rosenberg, S. A. Progress in human tumour immunology and immunotherapy. *Nature* 411, 380-4. (2001).

Ruddle, N. H. Lymphoid neo-organogenesis: lymphotoxin's role in inflammation and development. *Immunol Res* 19, 119-25 (1999).

Sarma, S. et al. Cytotoxic T lymphocytes to an unmutated tumor rejection antigen P1A: normal development but restrained effector function in vivo. *J* Exp Med 189, 811-20. (1999).

Schreiber, H. Tumor Immunology. in Fundamental Immunology (ed. Paul, W. E.) 1247-1280 (Lippincott Raven Press, New York, 1999).

Sha, W. C. et al. Selective expression of an antigen receptor on CD8-bearing T lymphocytes in transgenic mice. *Nature* 335, 271-4 (1988).

Tamada, K. et al. Modulation of T-cell-mediated immunity in tumor and graft-versus-host disease models through the LIGHT co-stimulatory pathway. *Nat Med* 6, 283-9. (2000).

Wang, J. et al. The complementation of lymphotoxin deficiency with LIGHT, a newly discovered TNF family member, for the restoration of secondary lymphoid structure and function. *Eur J Immunol* 32:1969 (2002).

Wang, J. et al. The regulation of T cell homeostasis and autoimmunity by T cell derived LIGHT. *J Clinic. Invest.* 108:1771-1780 (2001).

Wick, M. et al. Antigenic cancer cells grow progressively in immune hosts without evidence for T cell exhaustion or systemic anergy. *J Exp Med* 186, 229-38. (1997).

Wu, Q. et al. The requirement of membrane lymphotoxin for the presence of dendritic cells in lymphoid tissues. *J Exp Med* 190, 629-38 (1999).

Ye, Q. et al. Modulation of LIGHT-HVEM costimulation prolongs cardiac allograft survival. *J Exp Med* 195, 795-800. (2002).

Ye, Z. et al. Gene therapy for cancer using single-chain Fv fragments specific for 4-1BB. *Nat Med* 8, 343-8. (2002).

Zhai, Y. et al. LIGHT, a novel ligand for lymphotoxin beta receptor and TR2/HVEM induces apoptosis and suppresses in vivo tumor formation via gene transfer. *Journal of Clinical Investigation* 102, 1142-51 (1998).

Zinkernagel, R. M. Immunity against solid tumors? *Int J Cancer* 93, 1-5. (2001).

U.S. Pat. No. 6,048,551
U.S. Pat. No. 5,436,146
U.S. Pat. No. 4,980,286
U.S. Pat. No. 5,994,523
U.S. Pat. No. 6,207,147

I claim:

1. A protease resistant mutant LIGHT protein having the amino acid sequence of LIGHT with a protease site between the transmembrane domain and amino acid position 85 in the extracellular domain with a deletion in the protease site, wherein the mutant LIGHT protein is stably present on the surface of a tumor cell.

2. The mutant LIGHT protein of claim 1 is a recombinant protein.

3. The mutant LIGHT protein of claim 1 wherein the protease site is deleted.

4. The mutant LIGHT protein of claim 1, wherein the mutant LIGHT protein activates tumor-specific T-cells.

* * * * *